(12) United States Patent
Balu

(10) Patent No.: US 7,459,522 B2
(45) Date of Patent: *Dec. 2, 2008

(54) PEPTIDE DIMERS AS AGONISTS OF THE ERYTHROPOIETIN (EPO) RECEPTOR, AND ASSOCIATED METHODS OF SYNTHESIS AND USE

(75) Inventor: Palani Balu, Cupertino, CA (US)

(73) Assignee: Affymax, Inc., Palo Alto, CA (US)

( * ) Notice: Subject to any disclaimer, the term of this patent is extended or adjusted under 35 U.S.C. 154(b) by 667 days.

This patent is subject to a terminal disclaimer.

(21) Appl. No.: 10/737,245

(22) Filed: Dec. 15, 2003

(65) Prior Publication Data

US 2006/0270831 A1 Nov. 30, 2006

Related U.S. Application Data

(63) Continuation of application No. 09/449,064, filed on Nov. 24, 1999, now Pat. No. 6,703,480.

(51) Int. Cl.
C07K 7/00 (2006.01)
A61K 38/10 (2006.01)

(52) U.S. Cl. ............... 530/300; 530/334; 530/345; 530/317; 514/2; 514/12

(58) Field of Classification Search ............ 530/300, 530/334, 345, 317; 514/2, 12
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,612,132 A | 9/1986 | Wollenberg | |
| 4,640,835 A | 2/1987 | Shimizu et al. | |
| 4,670,417 A | 6/1987 | Iwasaki | |
| 4,677,195 A | 6/1987 | Hewick et al. | |
| 4,703,008 A | 10/1987 | Lin et al. | |
| 4,791,192 A | 12/1988 | Nakagawa | |
| 5,061,786 A | 10/1991 | Burnier | |
| 5,106,954 A | 4/1992 | Fibi et al. | |
| 5,143,854 A | 9/1992 | Pirrung et al. | |
| 5,270,170 A | 12/1993 | Schatz et al. | |
| 5,278,065 A | 1/1994 | D'Andrea | |
| 5,322,837 A | 6/1994 | Hewick et al. | |
| 5,369,014 A | 11/1994 | Brugnara et al. | |
| 5,399,551 A | 3/1995 | Ise et al. | |
| 5,424,186 A | 6/1995 | Fodor et al. | |
| 5,432,018 A | 7/1995 | Dower et al. | |
| 5,482,924 A | 1/1996 | Royet et al. | |
| 5,767,078 A | 6/1998 | Johnson et al. | |
| 5,770,358 A | 6/1998 | Dower et al. | |
| 5,773,569 A * | 6/1998 | Wrighton et al. ............ 530/300 |
| 5,830,851 A | 11/1998 | Wrighton et al. | |
| 5,986,047 A | 11/1999 | Wrighton et al. | |

| | | | |
|---|---|---|---|
| 6,703,480 B1 * | 3/2004 | Balu .................. 530/300 |

FOREIGN PATENT DOCUMENTS

| | | |
|---|---|---|
| AU | 712713 | 12/1996 |
| CA | 2021528 | 1/1991 |
| EP | 0148605 | 7/1985 |
| EP | 0427189 | 5/1991 |
| EP | 0428267 | 5/1991 |
| WO | WO 90/08822 | 8/1990 |
| WO | WO 90/15070 | 12/1990 |
| WO | WO 91/05867 | 5/1991 |
| WO | WO 93/23550 | 11/1993 |
| WO | WO 93/25221 | 12/1993 |

(Continued)

OTHER PUBLICATIONS

Amagnostou, et al., "Erythropoietin has a mitogenic and positive chemotactic effect on endothelial cells", Proc. Natl. Acad. Sci. USA 87: 5978-5982, (1990).
Ando, et al., "Regulation of G1/S transition by cyclins D2 and D3 in hematopoietic cells", Proc. Natl. Acad. Sci. USA 90: 9571-9575, (1993).
Barker, et al., "Cyclic RGD Peptide Analogues as antiplatelet Antithrombotics", J. Med. Chem. 35: 2040-2048, (1992).
Bodonsky, et al., "Active Esters and Resins in Peptide Synthesis", Chem. Ind. 38:1597, (1996).
Bowie, et al., "Deciphering the Message in Protein Sequences: Tolerance to Amino Acid Substitutions", Science 247:1306-1310, (1990).
Branch, et al., "Identification of an Erythoropoietin Sensitive Cell Line", Blood 69:1782-1785, (1987).

(Continued)

*Primary Examiner*—Chih-Min Kam
(74) *Attorney, Agent, or Firm*—Goodwin Procter LLP

(57) ABSTRACT

Novel peptide dimers are provided that bind and activate the erythropoietin receptor (EPO-R) or otherwise act as an EPO agonist. The novel compounds have a first peptide chain $R^1$ and a second peptide chain $R^2$, wherein $R^1$ and $R^2$ may be the same or different, and are linked through a linking moiety. $R^1$ is approximately 10 to 40 amino acid residues in length and comprises the sequence $X_3X_4X_5GPX_6TX_7X_8X_9$ (SEQ ID NO: 1) wherein $X_3$ is C or Hoc, $X_4$ is R, H, L or W, $X_5$ is M, F, I or nor-leucine (J), $X_6$ is any one of the 20 genetically coded L-amino acids or J, $X_7$ is W, 1-naphthylalanine (B) or 2-naphthylalanine (U), $X_8$ is D, E, I, L or V, and $X_9$ is C or Hoc. Similarly, $R^2$ comprises the sequence $X'_3X'_4X'_5GPX'_6TX'_7X'_8X'_9$ (SEQ IN NO: 2) wherein $X'_3$ is C or Hoc, $X'_4$ is R, H, L or W, $X'_5$ is M, F, I or J, $X'_6$ is any one of the 20 genetically coded L-amino acids or J, $X'_7$ is W, B or U, $X'_8$ is D, E, I, L or V, and $X'_9$ is C or Hoc. Methods for synthesizing the compounds are provided as well, as are pharmaceutical compositions and methods of use.

13 Claims, 8 Drawing Sheets

FOREIGN PATENT DOCUMENTS

| WO | WO 94/02611 | 2/1994 |
|---|---|---|
| WO | WO 95/11987 | 5/1995 |
| WO | WO 95/25746 | 9/1995 |
| WO | WO 96/40749 | 12/1996 |
| WO | WO 96/40772 | 12/1996 |
| WO | WO 01/38342 | 5/2001 |

OTHER PUBLICATIONS

Caras, et al., "Signal Peptide for Protein Secretion Directing Glycophospholip Membran Anchor Attachment", Science 243:1196-1198, (1989).

Claus-Walker, et al., "Spinal Cord Injury and Serum Erythropoietin", Arch. Phys. Med. Rehabil. 65:370-374, (1984).

Cotes, et al., "Changes in serum immunoreactive erythropoietin during the menstrual cycle and normal pregnancy", Brit. J. Obstetrics and Gynaecology, 90:305-311, (1983).

Cwirla, et al., "Peptides on phage: A vast library of peptides for identifying ligands", Proc. Natl. Acad. Sci. USA 87:6378-6382, (1990).

Dainak, et al., "Mechanisms of Abnormal Erythropoiesis in malignancy", Cancer 5, 1101-1106, (1983).

Dexter, et al., "Growth of Factor-Dependent Hematopoetic Precursor Cell Lines", J. Exp. Med. 152:1036-1047, (1980).

Dower, et al., The search for Molecular Diversity (II): Recombinant and synthetic randomized Peptide libraries: Ann. Rep. Med. Chem. 26:271-280, (1991).

Dunn, et al., "Serum Erythropoietin Titers During Prolonged Bedrest: Relevance to the "Anaemia" of space flight", Eur. J. Appl. Physiol. 52: 178-182, (1984).

Dusanter-Fourt, et al., "Erythropoitin induces the tyrosine Phosphorylation of its own receptor in human Erythropoietin-responsive cells", J. Biol. Chem. 287:10670-10678, (1992).

Eschbach, et al., "Correction of the Anemia of End-Stage Renal Disease with Recombinant human erythropoietin", N. Eng. J. Med. 316: 73-78, (1987).

Fodor, et al., "Light-Directed, Spatially addressable parallel chemical synthesis", Science, 251:767-773, (1991).

Graber, et al., "Erythropoietin and the control of red cell production", Ann. Rev. Med., 29:51-66, (1978).

Greenberger, et al., "Demonstration of permanent factor-dependent multipotential erythroid/neutrophil/basophil) hematopoietic progenitor cell lines", Proc. Natl. Acad. Sci. US 80:2931-2935, (1983).

Haga, et al., "Plasma Erythropoietin Concentrations during the early Anemia of Prematurity", Acta Paediatr. Scand., 72: 827-831, (1983).

Kaiho, et al., "Sensitive Assay Systems for Detection of Hemoglobin with 2,7-Diaminoflourence: Histochemistry and Colorimetry for Erythrodifferentiation", Anal. Biochem. 149:177-120, (1985).

Kitamura, et al., "Identification and Analysis of Human Erythropoietin Receptors on a Factor-Dependent Cell Line, TF-1", Blood 73(2):375-280, (1989).

Krantz, et al., "Specific Binding of Erythropoietin to spleen cells infected with the anemia Strain of friend virus", Proc. Natl. Acad. Sci. USA 81:7574-7578, (1984).

Krystal, Gerald "A Simple microassay for Erythropoietin based on H-thymidine Incorporation into Spleen calls from Phenylhydrazine Treated Mice", Exp. Hematol., 11(7):649-660, (1983).

Konishi, et al., "Trophic effect of Erythropoietin and other hematopoietic factors on central cholinergic neurons in vitro in vivo", Brain Res., 609: 29-35, (1993).

Landschulz, et al., "Erythropoietin receptors on murine erythroid colony-forming units: Natural History", Blood 73: 1476-1478, (1989).

Leonard, et al., "Dynamics of GATA Transcript factor expression during erythroid differentiation", Blood, 82: 1071-1079, (1993).

Lin, et al., "Expression of T Cell Antigen Receptor Heterodimers in a Lipid-Linked Form", Science, 249:677-679, (1990).

Lipschitz, et al., "Effect of Age Hematopoiesis in Man", Blood, 63:502-509, (1983).

Livnah, et al., "Functional Mimicry of a Protein Hormone by a Peptide Agonist: The Structure of the EPOR complex to 2.8Å", Science 273:464-471, (1996).

Mayeux, et al., "Murine erythroleukaemia cells (Friend cells) possess high-affinity binding sites for eryropoietin", FEBS Lett., 211: 229-233, (1987).

Merrifield "Solid Phase Peptide Synthesis. The Synthesis of a Teterapeptide", J. Am. Chem. Soc., 85:2149, (1963).

Miller, et al., "Plasma Levels of Immunoreactive Erythropoietin after acute blood loss in man", Brit. J. Haematol., 52: 545-590, (1982).

Morgan and Gainor, et al., "Approaches to the discovery of non-peptide lignads for peptide receptors and peptidase", Ann. Rep. Med. Chem., 24:243-252, (1989).

Mosmann "Rapid Colorimetric Assay for cellular growth and survival: Applications to Proliferation and Cytotoxicity Assays", J. Immunol. Methods, 65:55, (1983).

Mufson, et al., "Binding and Internalization of recombinant Human erythropoietin in Murine erythroid Precursors Cells", Blood, 69:1485-1490, (1987).

Yat Su, et al., "Cysteine Alkylation in unprotected peptides: Synthesis of a Carbavasopressin analogue by Intramolecular Cysteine Alkylation", J. Org. Chem., 56:3146-3149, (1991).

Cwirla, S.E., et al., Science, 276, Jun. 13, 1997, pp. 1696-1699.

Patel, et al., "Activation of two discrete signaling pathways by erythropoietin", J. biol. chem., 267:21300-21302, (1992).

Quelle, et al., Interleukin 3, Granulocyte Macrophage Colony-stimulating Factor, and Transfected Erythropoietin receptors mediate tyrosine phosphoryllation of a common cytosolic protein (pp 100) in FDC-ER cells, j. Biol. Chem., 267:17055-17060, (1992).

Quelle, et al., "Proliferative action of erythropoietin is associated with rapid protein tyrosine phosphorylation in responsive B65Ut. EP", J. Biol. Chem., 266:609-614, (1991).

Sakaguchi, et al., "The Expression of Functional Erythropoietin receptors on an Interleukin-3 dependent Cell line", Biochem. biophys. Res. Commun., 146:7-12, (1987).

Sasaki, et al., "Carbohydrate Structure of Erythropoietin expressed in Chinese hamster ovary cells by a human erythropoietin cDNA", J. Biol. Chem., 262:12059-12076, 1987.

Sawyer, et al., "Identification of the receptor for erythropoietin by cross-linking to friend virus-infected erythroid cells", Proc. Natl. Acad. Sci. USA, 84:3690-3694, 1987.

Sawyer, et al., "Binding and receptor-mediated endocytosis of erythropopietin in friend virsus-infected erythroid cells", J. Biol. Chem., 262:5554-5562, 1987.

Schwartz, et al., "Severe Anemia as a manifestation of metastitic jugular paraganglioma", Arch. Otolaryngol. 109:269-272, 1983.

Stewart, et al., solid Phase peptide synthesis pierce chemical co., Rockford, III, Table of Contents, 1984.

Todokoro, et al., "Specific binding of erythropoietin to its receptor on responsive mouse erythroleukemic cells", Proc. Natl. Acad. Sci. USA, 84:4126-4130, 1988.

Udupa, et al., "Erythropoiesis in the aged mouse", J. Lab.Clin. Med., 103:581-588, 1984.

Vedovato, et al., "Erythropoietin levels in heterozygous beta-thalassemia", Acta. Haematol., 71:211-213, 1984.

Vichinsky, et al., "Inadequate erythroid response to hypoxia in cystic fibrosis", J. Pediatric., 105:15-21, 1984.

Weinstein, et al., Peptide backbone modifications: A structure-activity analysis of peptides containing amide bond surrogates, conformational constraints, and related modifications, Chemistry & Biochemistry of amino Acids, Peptides and Proteins Marcel-Dekker: New York, 7:267, 1983.

Wells, et al., "Hormone Mimicry", Science, 273:449-450, (1996).

Willhuhn, et al., "JAK2 associated with the erythropoietin receptor and is tyrosine phosphorylated and activated following stimulation with Erythropoietin", Cell, 74:227-236, (1993).

Worthington, et al., "Quantitation of Erythroid Differentiation in vitro using a sensitive colorimetric assay for Hemoglobin", Exp. Hematol., 15:85-92, 1987.

Wrighton, et al., "Small peptides as potent mimics of the protein hormone erythropoietin", Science, 458-464, (1996).

Wrighton, et al., "Increased Potency of an erythropoietin peptide mimetic through covalent dimerization", Nature Biotechnology, 15:1261-1265, (1997).

* cited by examiner

| | |
|---|---|
| GGTYSCHFGPLTBVCRPQGG | SEQ ID NO: 7 |
| GGTYSCHFGPLTBVCRPQGGK | SEQ ID NO: 8 |
| GGTYSCHFGPLTBVCRPQ | SEQ ID NO: 9 |
| GTYSCHFGPLTBVCRPQ | SEQ ID NO: 10 |
| GGTYSCHFGPLTBVCJPQGG | SEQ ID NO: 11 |
| GGTYSCHFGPLTBVCQPLGG | SEQ ID NO: 12 |
| GGLYACHJGPJTBVCQPLRG | SEQ ID NO: 13 |
| GGLYACHMGPMTBVCQPLRG | SEQ ID NO: 14 |
| GGTYSCHFGPLTBVCRPQGG | SEQ ID NO: 15 |
| GGLYLCRFGPVTBDCGYKGG | SEQ ID NO: 16 |
| VGNYMCHFGPITBVCRPGGG | SEQ ID NO: 17 |
| GGVYACRMGPITBVCSPLGG | SEQ ID NO: 18 |
| GGPHHVYACRMGPLTBIC | SEQ ID NO: 19 |
| TIAQYICYMGPETBECRPSPKA | SEQ ID NO: 20 |
| YCHFGPLTBVC | SEQ ID NO: 21 |
| YSCHFGPLTBVCK | SEQ ID NO: 22 |
| GGTYSCHFGPLTBVCKPQ | SEQ ID NO: 23 |
| GGDYHCRMGPLTBVCKPLGG | SEQ ID NO: 24 |
| GGTYSCHFGPLTBVCKPQGG | SEQ ID NO: 25 |
| GGTYSCHFGPLTUVCRPQGG | SEQ ID NO: 26 |
| GGTYRCSMGPMTBVCLPMGG | SEQ ID NO: 27 |
| GGMYSCRMGPMTBVCGPSGG | SEQ ID NO: 28 |
| GGWAWCRMGPITBVCSAHGG | SEQ ID NO: 29 |
| GGMYSCRMGPMTBVCIPYGG | SEQ ID NO: 30 |
| GGEYKCYMGPITBVCKPEGG | SEQ ID NO: 31 |
| GGDYTCRMGPMTBICTATGG | SEQ ID NO: 32 |
| GGNYLCRFGPGTBDCTGFRG | SEQ ID NO: 33 |
| GGNYVCRMGPITBICTPAGG | SEQ ID NO: 34 |
| GGKDVCRMGPITBDCRSTGG | SEQ ID NO: 35 |
| GGSYLCRMGPTTBLCTAQRGGGN | SEQ ID NO: 36 |
| GGNYLCRMGPATBVCGRMGG | SEQ ID NO: 37 |
| GGEYKCRMGPLTBVCQYAGG | SEQ ID NO: 38 |
| GGDYTCRMGPMTBICTATRG | SEQ ID NO: 39 |
| GGVYVCRMGPLTBECTASGG | SEQ ID NO: 40 |

Figure 1-1

| | |
|---|---|
| GGEYSCRMGPMTBVCSPTGG | SEQ ID NO: 41 |
| GGEYLCRMGPITBVCERYGG | SEQ ID NO: 42 |
| GGNYICRMGPMTBVCTAHGG | SEQ ID NO: 43 |
| GGDYLCRMGPATBVCGRMGG | SEQ ID NO: 44 |
| GGLYSCRMGPITBVCTKAGG | SEQ ID NO: 45 |
| GGGYHCRMGPMTBVCRPVGG | SEQ ID NO: 46 |
| GGIYKCLMGPLTBVCTPDGG | SEQ ID NO: 47 |
| GGLYSCLMGPITBLCKPKGG | SEQ ID NO: 48 |
| GGDYSCRMGPTTBVCTPPGG | SEQ ID NO: 49 |
| GGDYWCRMGPSTBECNAHGG | SEQ ID NO: 50 |
| GGKYLCSFGPITBVCARYGG | SEQ ID NO: 51 |
| GGLYKCRLGPITBVCSPLGG | SEQ ID NO: 52 |
| GGSYTCRFGPETBVCRPNGG | SEQ ID NO: 53 |
| GGSYSCRMGPITBVCKPGGG | SEQ ID NO: 54 |
| GGSYTCRMGPITBVCLPAGG | SEQ ID NO: 55 |
| GGLYECRMGPMTBVCRPGGG | SEQ ID NO: 56 |
| GGDYTCRMGPITBICTKAGG | SEQ ID NO: 57 |
| GGVYSCRMGPTTBECNRYVG | SEQ ID NO: 58 |
| GGAYLCHMGPITBVCRPQGG | SEQ ID NO: 59 |
| GGEYSCRMGPNTBVCKPVGG | SEQ ID NO: 60 |
| GGLYLCRMGPVTBECQPRGG | SEQ ID NO: 61 |
| GGLYTCRMGPITBVCLLPGG | SEQ ID NO: 62 |
| GGLYTCRMGPVTBVCTGAGG | SEQ ID NO: 63 |
| GGVYKCRMGPLTBECRPTGG | SEQ ID NO: 64 |
| GGDYNCRFGPLTBVCKPSGG | SEQ ID NO: 65 |
| GGSYLCRFGPTTBLCSSAGG | SEQ ID NO: 66 |
| GGSYLCRMGPTTBVCTRMGG | SEQ ID NO: 67 |
| GGSYLCRFGPTTBLCTQRGG | SEQ ID NO: 68 |
| GGWVTCRMGPITBVCGVHGG | SEQ ID NO: 69 |
| GGQLLCGIGPITBVCRWVGG | SEQ ID NO: 70 |
| GGKYSCFMGPTTBVCSPVGRGV | SEQ ID NO: 71 |
| GGWVYCRIGPITBVCDTNGG | SEQ ID NO: 72 |
| GGMYYCRMGPMTBVCKGAGG | SEQ ID NO: 73 |
| GGTTQCWIGPITBVCRARGG | SEQ ID NO: 74 |

Figure 1-2

| | |
|---|---|
| GGPYHCRMGPITBVCGPVGG | SEQ ID NO: 75 |
| GGEYRCRMGPISBVCSPQGG | SEQ ID NO: 76 |
| GGNYTCRFGPLTBECTPQGGGA | SEQ ID NO: 77 |
| GGSWDCRIGPITBVCKWSGG | SEQ ID NO: 78 |
| GGLYLCRMGPQTBMCQPGGG | SEQ ID NO: 79 |
| GGDYVCRMGPMTBVCAPYGR | SEQ ID NO: 80 |
| GGWYSCLMGPMTBVCKAHRG | SEQ ID NO: 81 |
| GGKYYCWMGPMTBVCSPAGG | SEQ ID NO: 82 |
| GGYVMCRIGPITBVCDIPGG | SEQ ID NO: 83 |
| GSCLQCCIGPITBVCRHAGG | SEQ ID NO: 84 |
| GGNYFCRMGPITBVCQRSVG | SEQ ID NO: 85 |
| GGEYICRMGPLTBECKRTGG | SEQ ID NO: 86 |
| GGLYACRMGPITBVCKYMAG | SEQ ID NO: 87 |
| GGQYLCTFGPITBLCRGAGG | SEQ ID NO: 88 |
| GGYTCRMGPITBVCSAHGG | SEQ ID NO: 89 |
| GGTYKCWMGPMTBVCRPVGG | SEQ ID NO: 90 |
| GGNYYCRFGPITFECHPTGG | SEQ ID NO: 91 |
| GGEYLCRMGPMTBVCTPVGG | SEQ ID NO: 92 |
| GGLYTCRMGPITBVCLPAGG | SEQ ID NO: 93 |

Figure 1-3

ISOMER 1

ISOMER 2

ISOMER 3

PEPTIDE DIMERS AS AGONISTS OF THE ERYTHROPOIETIN (EPO) RECEPTOR, AND ASSOCIATED METHODS OF SYNTHESIS AND USE

This application claims priority as a continuation application of Balu, U.S. patent application Ser. No. 09/449,064, filed Nov. 24, 1999, now U.S. Pat. No. 6,703,480, titled the same, and the disclosure of which is herein incorporated by reference in its entirety, including drawings and sequence listing.

TECHNICAL FIELD

The present invention provides novel compounds that bind to and activate the erythropoietin (EPO) receptor or otherwise act as EPO agonists. The invention additionally relates to methods for synthesizing the novel compounds, methods of using the novel compounds, and pharmaceutical compositions containing a compound of the invention as the active agent. The invention has application in the fields of biochemistry and medicinal chemistry and particularly provides EPO agonists for use in the treatment of human disease.

BACKGROUND

Erythropoietin (EPO) is a glycoprotein hormone with 165 amino acids, 4 glycosylation sites on amino-acid positions 24, 38, 83, and 126, and a molecular weight of about 34,000. It is initially produced as a precursor protein with a signal peptide of 23 amino acids. EPO can occur in three forms: α, β, and asialo. The α and β forms differ slightly in the carbohydrate components, but have the same potency, biological activity, and molecular weight. The asialo form is an α or β form with the terminal carbohydrate (sialic acid) removed. The DNA sequences encoding EPO have been reported. See, Lin (1987) U.S. Pat. No. 4,703,008.

EPO stimulates mitotic division and the differentiation of erythrocyte precursor cells and thus ensures the production of erythrocytes. It is produced in the kidney when hypoxic conditions prevail. During EPO-induced differentiation of erythrocyte precursor cells, there is induction of globin synthesis and increases in the synthesis of the heme complex and in the number of ferritin receptors. This makes it possible for the cell to take on more iron and synthesize functional hemoglobin. Hemoglobin in mature erythrocytes binds oxygen. Thus, the erythrocytes and the hemoglobin contained in them play a key part in supplying the body with oxygen. The complex processes which have been described are initiated by the interaction of EPO with an appropriate receptor on the cell surface of the erythrocyte precursor cells. See, e.g., Graber and Krantz (1978) Ann. Rev. Med. 29:51-66.

EPO is present in very low concentrations in plasma when the body is in a healthy state wherein tissues receive sufficient oxygenation from the existing number of erythrocytes. This normal low concentration is enough to stimulate replacement of red blood cells which are lost normally through aging.

The amount of EPO in the circulation is increased under conditions of hypoxia when oxygen transport by blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. In response to tissues undergoing hypoxic stress, EPO will increase red blood cell production by stimulation of proliferation of erythroid progenitor cells. When the number of red blood cells in circulation is greater than needed for normal tissue oxygen requirements, EPO in circulation is decreased.

Because EPO is essential in the process of red blood cell formation, the hormone has potentially useful applications in both the diagnosis and the treatment of blood disorders characterized by low or defective red blood cell production. Recent studies have provided a basis for the projection of efficacy of EPO therapy in a variety of disease states, disorders, and states of hematologic irregularity, including: beta-thalassemia (see, Vedovato et al. (1984) Acta. Haematol. 71:211-213); cystic fibrosis (see Vichinsky et al. (1984) J. Pediatric. 105:15-21; pregnancy and menstrual disorders (see Cotes et al. (1993) Brit. J. Obstet. Gyneacol. 90:304-311; early anemia of prematurity (see Haga et al. (1983) Acta Pediatr. Scand. 72:827-831); spinal cord injury (see Claus-Walker et al. (1984) Arch. Phys. Med. Rehabil. 65:370-374); space flight (see Dunn et al. (1984) Eur. J. Appl. Physiol. 52:178-182); acute blood loss (see Miller et al. (1982) Brit. J. Haematol. 52:545-590); aging (see Udupa et al. (1984) J. Lab. Clin. Med. 103:574-580 and 581-588 and Lipschitz et al. (1983) Blood 63:502-509; various neoplastic disease states accompanied by abnormal erythropoiesis (see Dainiak et al. (1983) Cancer 5:1101-1106 and Schwartz et al. (1983) Otolaryngol. 109:269-272); and renal insufficiency (see Eschbach et al. (1987) N. Eng. J. Med. 316:73-78).

Purified, homogeneous EPO has been characterized. See Hewick, U.S. Pat. No. 4,677,195. A DNA sequence encoding EPO was purified, cloned and expressed to produce synthetic polypeptides with the same biochemical and immunological properties. A recombinant EPO molecule with oligosaccharides identical to those on the natural material has also been produced. See, Sasaki et al. (1987) J. Biol. Chem. 262:12059-12076.

Despite the availability of purified recombinant EPO, little is known concerning the mechanism of EPO-induced erythroblast proliferation and differentiation. The specific interaction of EPO with progenitors of immature red blood cells, platelets, and megakaryocytes remains to be characterized. This is due, at least in part, to the small number of surface EPO receptor molecules on normal erythroblasts and on the erythroleukemia cell line. See, Krantz and Goldwasser (1984) Proc. Natl. Acad. Sci. USA 81:7574-7578; Branch et al. (1987) Blood 69:1782-1785; Mayeux et al. (1987) FEBS Letters 211:229-233; Mufson and Gesner (1987) Blood 69:1485-1490; Sakaguchi et al. (1987) Biochem. Biophys. Res. Commun. 146:7-12; Sawyer et al. (1987) Proc. Natl. Acad. Sci. USA 84:3690-3694; Sawyer et al. (1987) J. Biol. Chem. 262:5554-5562; and Todokoro et al. (1988) Proc. Natl. Acad. Sci. USA 84:4126-4130.

Cross-linked complexes between radioiodinated EPO and cell surface proteins suggest that the cell surface proteins comprise two polypeptides having approximate molecular weights of 85,000 daltons and 100,000 daltons, respectively. More recently, the two cross-linked complexes have been subjected to V8 protease digestion and have been found to have identical peptide fragments, suggesting that the two EPO-binding polypeptides may be products of the same or very similar genes. See, Sawyer et al. (1988) supra. Most cell surface binding studies, however, have revealed a single class of binding sites, averaging 300 to 600 per cell surface, with a Kd of approximately 800 pM (picomolar). See, Sawyer et al. (1987) Proc. Natl. Acad. Sci. USA 84:3690-3694. However, EPO-responsive splenic erythroblasts, prepared from mice injected with the anemic strain (FVA) of the Friend leukemia virus, demonstrate a high and a low affinity binding site with dissociation constants of 100 pM and 800 pM, respectively. See, Sawyer et al. (1987) J. Biol. Chem. 262:5554-5562 and Landschulz (1989) *Blood* 73:1476-1478. The DNA sequences and encoded peptide sequences for murine and human EPO receptor proteins have been described. See, D'Andrea et al., PCT Patent Publication No. WO 90/08822 (published 1990).

The availability of cloned genes for the EPO receptor (EPO-R) facilitates the search for agonists and antagonists of this important receptor. The availability of the recombinant receptor protein allows the study of receptor-ligand interaction in a variety of random and semi-random peptide diversity generation systems. These systems include the "peptides on plasmids" system described in U.S. patent application Ser. No. 778,233, filed Oct. 16, 1991, issued as U.S. Pat. No. 5,270,170, the "peptides on phage" system described in U.S. patent application Ser. No. 718,577, issued as U.S. Pat. No. 5,432,018 and in Cwirla et al., August 1990, *Proc. Natl. Acad. Sci. USA* 87:6378-6382, the "encoded synthetic library" (ESL) system described in U.S. patent application Ser. No. 946,239, filed Sep. 16, 1992, which is a continuation-in-part application of Ser. No. 762,522, filed Sep. 18, 1991, now abandoned, the "very large scale immobilized polymer synthesis" system described in U.S. patent application Ser. No. 492,462, filed Mar. 7, 1990, now U.S. Pat. No. 5,143,854, and those systems described in PCT patent publication No. 90/15070, published Dec. 13, 1990, U.S. patent application Ser. No. 624,120, filed Dec. 6, 1990, now abandoned, Fodor et al., 15 Feb. 1991, *Science* 251:767-773, Dower and Fodor, 1991, *Ann. Rep. Med. Chem.* 26:271-180, and U.S. patent application Ser. No. 805,727, filed Dec. 6, 1991, now U.S. Pat. No. 5,424,186.

Novel peptides that interact with the EPO-R have been discovered, and have been disclosed in U.S. Pat. No. 5,773, 569 to Wrighton et al. The Wrighton et al. peptides are generally single polypeptide chains about 10 to 40 amino acids in length, and contain a pair of cysteine residues separated by eight amino acids. These EPO-R-binding peptides were found to bind to or otherwise interact with the EPO-R, and were thus presumed to be useful for studying the biological activities of the EPO-R and for treatment of disease involving a deficiency of EPO. A related patent, U.S. Pat. No. 5,830,851 to Wrighton et al., pertains more specifically to therapeutic applications of the aforementioned peptides, and focuses on the use of the compounds to treat disorders such as end-stage renal failure or dialysis, anemia associated with AIDS, autoimmune diseases, malignancies, and chronic inflammatory disease, beta-thalassemia, cystic fibrosis, spinal cord injury, acute blood loss, aging, and neoplastic disease states accompanied by abnormal erythropoiesis.

There remains a need, however, for highly active compounds that bind very specifically to the EPO-R, both for studies of the important biological activities mediated by the receptor and for treatment of diseases, disorders and conditions associated with an EPO deficiency. There remains a further need for improved synthetic methods for the production of such compounds. The present invention provides such compounds and methods, and also provides pharmaceutical compositions and methods for using the compounds as therapeutic agents.

SUMMARY OF THE INVENTION

In one embodiment, the invention provides compounds in the form of peptide dimers that bind to and activate the EPO-R or otherwise behave as EPO agonists. The compounds have a first peptide chain $R^1$ and a second peptide chain $R^2$, wherein $R^1$ and $R^2$ may be the same or different, and are linked through a linking moiety. $R^1$ is approximately 10 to 40 amino acid residues in length and comprises a core sequence of amino acids $X_3X_4X_5GPX_6TX_7X_8X_9$ (SEQ ID NO: 1) wherein each amino acid is indicated by standard one-letter abbreviation, $X_3$ is C or homocysteine (Hoc), $X_4$ is R, H, L or W, $X_5$ is M, F, I or nor-leucine (J), $X_6$ is selected from any one of the 20 genetically coded L-amino acids and J, $X_7$ is W, 1-naphthylalanine (also referred to herein as "1-Nal" or B) or 2-naphthylalanine (also referred to herein as "2-Nal" or U), $X_8$ is D, E, I, L or V, and $X_9$ is C or Hoc. $R^2$ is also approximately 10 to 40 amino acid residues in length and, similarly, comprises a core sequence of amino acids $X'_3X'_4X'_5GPX'_6TX'_7X'_8X'_9$ is C or (SEQ ID NO: 2) wherein each amino acid is indicated by standard one-letter abbreviation, $X'_3$ is C or Hoc, $X'_4$ is R, H, L or W, $X'_5$ is M, F, I or J, $X'_6$ is selected from any one of the 20 genetically coded L-amino acids and J, $X'_7$ is W, B or U, $X_8'$ is D, E, I, L or V, and $X'_9$ is C or Hoc. The linker moiety between $R^1$ and $R^2$ is preferably although not necessarily a $C_{1\text{-}2}$ linking moiety optionally terminated with one or two —NH— linkages and optionally substituted at one or more available carbon atoms with a lower alkyl substituent. In addition, a β-alanine residue may be present between $R^1$ and the linking moiety, or between $R^2$ and the linking moiety, or both. Generally, although not necessarily, either (a) $X_3$ and $X_9$ are linked by a disulfide bond and $X'_3$ and $X'_9$ are linked by a disulfide bond, (b) $X_3$ and $X'_9$ are linked by a disulfide bond and $X'_3$ and $X_9$ are linked by a disulfide bond, or (c) $X_3$ and $X'_3$ are linked by a disulfide bond and $X'_9$ and $X_9$ are linked by a disulfide bond.

More preferably, $R^1$ comprises a core sequence of amino acids $YX_2X_3X4X_5GPX6TBX_8X_9X_{10}$ (SEQ ID NO: 3) wherein $X_2$, $X_6$ and $X_{10}$ are independently selected from any one of the 20 genetically coded L-amino acids, $X_3$ is C or Hoc, $X_4$ is R, H or L, $X_5$ is M, F or I, $X_8$ is D, E, I, L or V, and $X_9$ is C or Hoc. $R^2$ comprises a core sequence of amino acids $YX'_2X'_3X'_4X'_5GPX'_6TBX'_8X'_9X'_{10}$ (SEQ ID NO: 4) wherein $X'_2$, $X'_6$ and $X'_{10}$ are independently selected from any one of the 20 genetically coded L-amino acids, $X'_3$ is C or Hoc, $X'_4$ is R, H or L, $X'_5$ is M, F or I, $X_8'$ is D, E, I, L or V, and $X'_9$ is C or Hoc, and the dimer contains two disulfide bonds.

In a most preferred embodiment, $R^1$ comprises a core sequence of amino acids $X_1YX_2CX_4X_5GPX_6TBX_8CX_{10}X_{11}X_{12}$ (SEQ ID NO: 5) wherein $X_1$, $X_2$, $X_6$, $X_1$ and $X_{12}$ are independently selected from any one of the 20 genetically coded L-amino acids, $X_4$ is R or H, $X_5$ is M or F, $X_8$ is D, E, I, L or V, and $X_{10}$ is R; $R^2$ comprises a core sequence of amino acids $X'_1YX'_2CX'_4X'_5GPX'_6TBX'_8CX'_{10}GX'_{11}X'_{12}$ (SEQ ID NO: 6) wherein $X'_1$, $X'_2$, $X'_6$, $X'_{11}$ and $X'_{12}$ are independently selected from any one of the 20 genetically coded L-amino acids, $X'_4$ is R or H, $X'_5$ is M or F, $X_8'$ is D, E, I, L or V, and $X'_{10}$ is R, wherein $R^1$ and $R^2$ are identical; the thiol functionalities of $X_3$ and $X_9$ are linked to form an intramolecular disulfide bond within the $R^1$ and, similarly, the thiol functionalities of $X_3'$ and $X_9'$ are linked to form an intramolecular disulfide bond within $R^2$; the linker comprises —NH—$R^3$—NH— wherein $R^3$ is lower ($C_{1-6}$) alkylene substituted with a functional group such as a carboxyl group that enables binding to another molecular moiety (e.g., as may be present on the surface of a solid support), and is optionally substituted with a lower alkyl group; and a β-alanine residue is present between $R^1$ and the linker and/or between $R^2$ and the linker. Optimally, the linker is a lysine residue.

According to some embodiments of this invention, two or more, and preferably between two and six amino acid residues, independently selected from any of the 20 genetically coded L-amino acids or the stereoisomeric D-amino acids, will be coupled to the free (amino) terminus of $R^1$ and/or $R^2$, i.e., the terminus of the peptide chain that is not bound to the linker. In addition, or in the alternative, such amino acid residues will be present at the opposing terminus of $R^1$ and/or $R^2$, i.e., between $R^1$ and/or $R^2$ and the β-alanine group, if one is present, or between $R^1$ and/or $R^2$ and the linker moiety, if no β-alanine group is present. For example, the sequence GG will often be appended to termini of the core sequences for ease in synthesis of the peptides. Other modifications are also possible, including capping or otherwise modifying the free amino terminus of $R^1$ and/or $R^2$, replacement of one or more of the naturally occurring, genetically encoded amino acids with a synthetic amino acid, peptide phosphorylation, modification of an amino acid side chain, and the like. Particularly preferred modification comprises covalent attachment of polyethylene glycol moieties at the N-terminus of both $R^1$ and $R^2$.

The invention also provides a method for synthesizing the aforementioned dimer compounds wherein each of $R^1$ and $R^2$ independently contains a cyclic moiety deriving from an intramolecular disulfide bond formed between two cysteine or homocysteine residues. The method is preferably a one-step oxidation process which preferentially results in the desired compound, i.e., a dimer with each peptide chain containing an intramolecular cyclic structure, and minimizes the less desirable (i.e., less active) products in which disulfide bridges are present linking $R^1$ and $R^2$.

The present invention also provides methods for treating disease involving a deficiency of EPO utilizing the novel compounds of the invention, and further provides pharmaceutical compositions comprising one or more compounds of the invention and a physiologically acceptable carrier.

BRIEF DESCRIPTION OF THE DRAWINGS

FIGS. 2-1 and 2-2 illustrate the synthetic scheme for preparation of a dimeric peptide of the invention using sequential synthesis of the chains and regioselective oxidation.

FIG. 3 illustrates a preferred synthetic scheme for preparation of a dimeric peptide of the invention, wherein the two peptide chains are synthesized simultaneously and a one-step "oxidative folding" technique is used to promote cyclization within each peptide chain.

DETAILED DESCRIPTION OF THE INVENTION

Figures 1, 2:
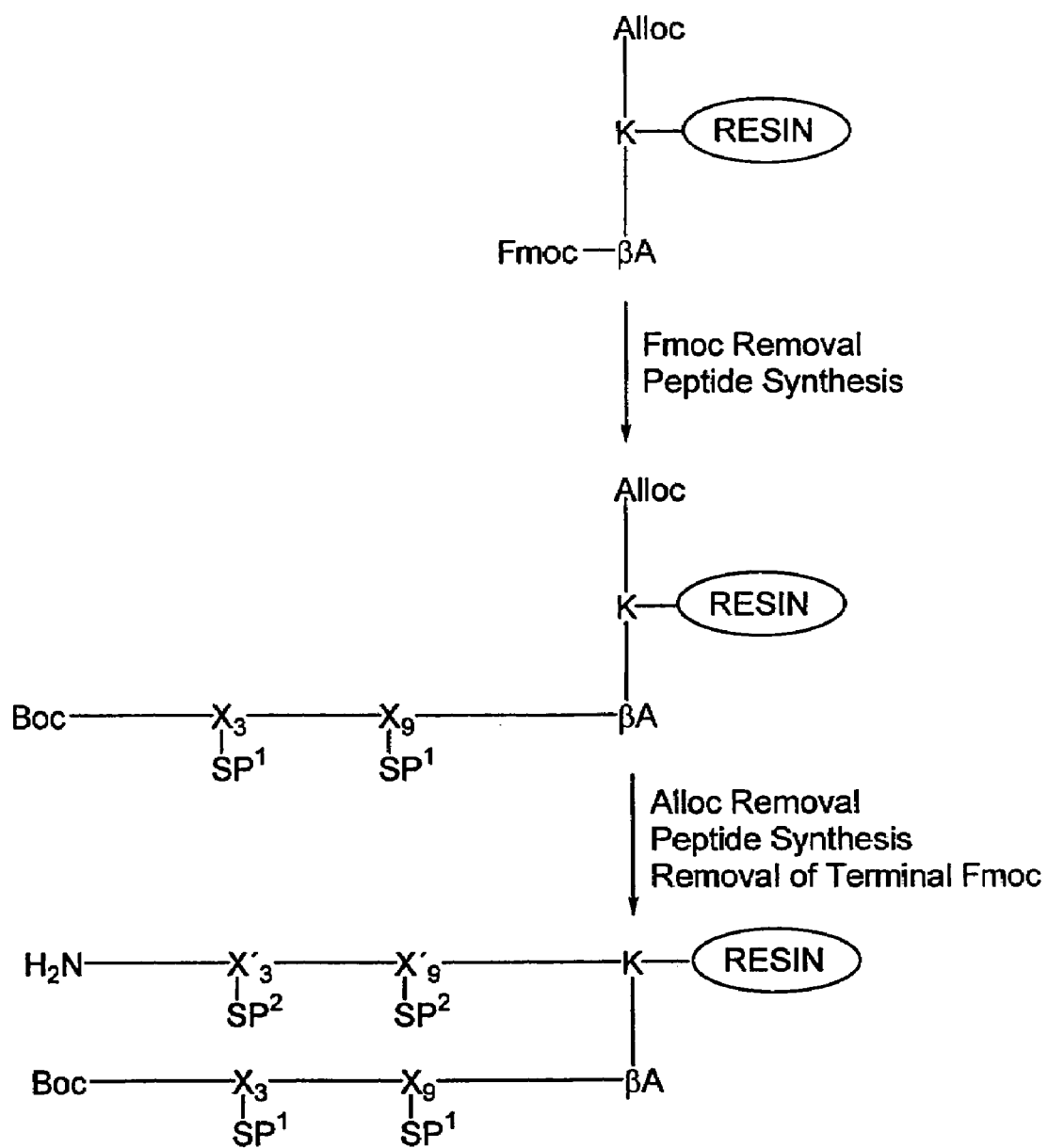
FIGS. 1-1, 1-2 and 1-3 provide the sequences of representative $R^1$ and $R^2$ peptide chains contained within the dimers of the invention.
Figure 2:
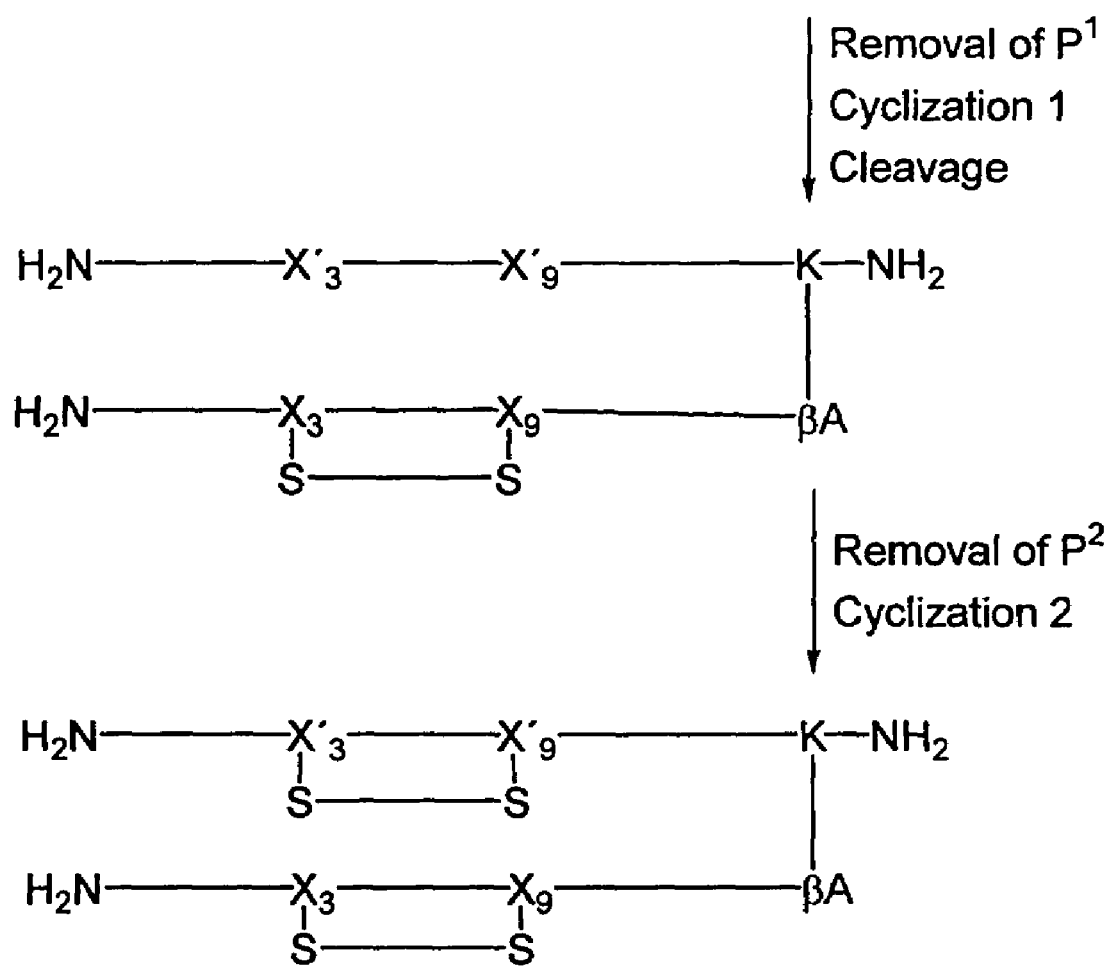

I. Definitions and Overview:

It is to be understood that unless otherwise indicated, this invention is not limited to specific peptide sequences, molecular structures, pharmaceutical compositions, methods of synthesis, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a novel compound" in a pharmaceutical composition means that more than one of the novel compounds can be present in the composition, reference to "a pharmaceutically acceptable carrier" includes combinations of such carriers, and the like.

In this specification and in the claims which follow, reference will be made to a number of terms which shall be defined to have the following meanings:

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. In addition, the letter "B" is used to refer to 1-naphthylalanine (also sometimes referred to herein as "1-Nal"), the letter "U" is used to refer to 2-naphthylalanine (also sometimes referred to herein as "2-Nal"), and the letter "J" is used to refer to nor-leucine.

Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for compounds of the present invention. Examples of unconventional amino acids include: β-alanine, 1-naphthylalanine, 2-naphthylalanine, 3-pyridylalanine, 4-hydroxyproline, O-phosphoserine, N-acetylserine, N-formylmethionine, 3-methylhistidine, 5-hydroxylysine, nor-leucine, and other similar amino acids and imino acids (e.g., 4-hydroxyproline).

"Peptide" or "polypeptide" refers to a polymer in which the monomers are alpha amino acids joined together through amide bonds. Peptides are two or often more amino acid monomers long.

The term "dimer" as in a peptide "dimer" refers to a compound in which two peptide chains are linked; generally, although not necessarily, the two peptide chains will be identical and are linked through a linking moiety covalently bound to the carboxyl terminus of each chain.

"Agonist" refers to a biologically active ligand which binds to its complementary biologically active receptor and activates the latter either to cause a biological response in the receptor, or to enhance preexisting biological activity of the receptor.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like.

"Pharmaceutically or therapeutically effective dose or amount" refers to a dosage level sufficient to induce a desired biological result. That result can be alleviation of the signs, symptoms, or causes of a disease, or any other desired alteration of a biological system. Preferably, this dose or amount will be sufficient to stimulate the EPO-R and, thus, alleviate the symptoms associated with a deficiency of EPO, or a defective or low red blood population in vivo.

The term "treat" as in "to treat a disease" is intended to include any means of treating a disease in a mammal, including (1) preventing the disease, i.e., avoiding any clinical symptoms of the disease, (2) inhibiting the disease, that is, arresting the development or progression of clinical symptoms, and/or (3) relieving the disease, i.e., causing regression of clinical symptoms.

The terms "disease," "disorder" and "condition" are used interchangeably herein to refer to a physiological state associated with a deficiency of EPO.

"Optional" or "optionally" means that the subsequently described circumstance may or may not occur, so that the description includes instances where the circumstance occurs and instances where it does not.

By "pharmaceutically acceptable carrier" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmaceutically acceptable" salt of a novel compound as provided herein is a salt or ester which is not biologically or otherwise undesirable.

II. The Novel Compounds:

In a first embodiment, the invention provides compounds that bind to and activate the EPO-R or otherwise behave as an EPO agonist. The compounds have the structure of formula (I)

wherein $R^1$, $R^2$, n1, n2 and LK are defined as follows.

$R^1$ is a peptide approximately 10 to 40 amino acid residues in length that comprises a core sequence of amino acids $X_3X_4X_5GPX_6TX_7X_8X_9$ (SEQ ID NO: 1) wherein each amino acid is indicated by standard one-letter abbreviation; $X_3$ is C or Hoc; $X_4$ is R, H, L or W; $X_5$ is M, F, I or J; $X_6$ is selected from any one of the 20 genetically coded L-amino acids and J; $X_7$ is W, B or U; $X_8$ is D, E, I, L or V; and $X_9$ is C or Hoc.

$R^2$ is also a peptide approximately 10 to 40 amino acid residues in length and, similarly, comprises a core sequence of amino acids $X'_3X'_4X'_5GPX'_6TX'_7X'_8X'_9$ (SEQ ID NO: 2) wherein each amino acid is indicated by standard one-letter abbreviation; $X'_3$ is C or Hoc; $X'_4$ is R, H, L or W; $X'_5$ is M, F, I or J; $X'_6$ is selected from any one of the 20 genetically coded L-amino acids and J; $X'_7$ is W, B or U; $X_8'$ is D, E, I, L or V; and $X'_9$ is C or Hoc.

The β-alanine ("βA") residues may or may not be present, meaning that n1 and n2 are independently zero or 1.

$L_K$ is a $C_{1-12}$ linking moiety optionally terminated with one or two —NH— linkages and optionally substituted at one or more available carbon atoms with a lower alkyl substituent. Preferably the linker $L_K$ comprises —NH—$R^3$—NH— wherein $R^3$ is lower ($C_{1-6}$) alkylene substituted with a functional group such as a carboxyl group or an amino group that enables binding to another molecular moiety (e.g., as may be present on the surface of a solid support), and is optionally substituted with a lower alkyl group. Optimally, the linker $L_K$ is a lysine residue or lysine amide, i.e., a lysine residue wherein the carboxyl group has been converted to an amide moiety —$CONH_2$.

The cysteine or homocysteine residues at $X_3$, $X_9$, $X'_3$, and $X'_9$ may contain free thiol groups, or disulfide bonds may be present linking these residues. Typically, the dimer contains two disulfide bonds, wherein either (a) $X_3$ and $X_9$ are linked by a disulfide bond and $X'_3$ and $X'_9$ are linked by a disulfide bond, (b) $X_3$ and $X'_9$ are linked by a disulfide bond and $X'_3$ and $X_9$ are linked by a disulfide bond, or (c) $X_3$ and $X'_3$ are linked by a disulfide bond and $X'_9$ and $X_9$ are linked by a disulfide bond. Option (a) is preferred, such that each peptide chain contains a cyclic group.

In addition, the amino terminus of $R^1$ (i.e., the terminus opposite the carboxyl terminus, which is bound directly or indirectly to the linker), the amino terminus of $R^2$, or both, may be modified by acetylation (with, for example, acetic acid, or a halogen-substituted acetic acid), or by coupling to a polyethylene glycol moiety.

In a more preferred embodiment, with respect to the peptide chains, $R^1$ comprise a core sequence of amino acids $YX_2X_3X_4X_5GPX_6TBX_8X_9X_{10}$ (SEQ ID NO: 3) wherein $X_2$, $X_6$ and $X_{10}$ are independently selected from any one of the 20 genetically coded L-amino acids, $X_3$ is C or Hoc, $X_4$ is R, H or L, $X_5$ is M, F or I, $X_8$ is D, E, I, L or V, and $X_9$ is C or Hoc, and $R^2$ comprise a core sequence of amino acids $YX'_2X'_3X'_4X'_5GPX'_6TBX'_8X'_9X'_{10}$ (SEQ ID NO: 4) wherein $X'_2$, $X'_6$ and $X'_{10}$ are independently selected from any one of the 20 genetically coded L-amino acids, $X'_3$ is C or Hoc, $X'_4$ is R, H or L, $X'_5$ is M, F or I, $X_8'$ is D, E, I, L or V, and $X'_9$ is C or Hoc. It is also preferred, although not essential, that $R^1$ and $R^2$ be identical.

In a most preferred embodiment: $R^1$ comprises a core sequence of amino acids $X_1YX_2CX_4X_5GPX_6TBX_8CX_{10}X_{11}X_{12}$ (SEQ ID NO: 5) wherein $X_1$, $X_2$, $X_6$, $X_{11}$ and $X_{12}$ are independently selected from any one of the 20 genetically coded L-amino acids, $X_4$ is R or H, $X_5$ is M or F, $X_8$ is D, E, I, L or V, and $X_{10}$ is R; $R^2$ comprises a core sequence of amino acids $X'_1YX'_2CX'_4X'_5GPX'_6TBX'_8CX'_{10}X'_{11}X'_{12}$ (SEQ ID NO: 6) wherein $X'_1$, $X'_2$, $X'_6$, $X'_{11}$, $X'_{12}$ are independently selected from any one of the 20 genetically coded L-amino acids, $X'_4$ is R or H, $X'_5$ is M or F, $X_8'$ is D, E, I, L or V, and $X'_{10}$ is R; $R^1$ and $R^2$ are identical; the two cysteine residues in each of $R^1$ and $R^2$ are linked to form a disulfide bond (so that each peptide chain contains a cyclic group); no lysine residues are present; and polyethylene glycol molecules are coupled to both $R^1$ and $R^2$ at the amino terminus of each chain.

Relative to the EPO-R agonists that have been previously disclosed, for example in U.S. Pat. No. 5,773,659 to Wrighton et al., the dimers of the invention are surprisingly more active. This appears to be due in part to the advantageous substitution of a 1-naphthylalanine residue (B) for tryptophan (W) (as disclosed in the aforementioned patent) at $X_7$ and $X'_7$, which provides for a six-fold more potent EPO agonist, in part to the two amino-terminal polyethylene glycol molecules in preferred compounds, which have been found to dramatically increases serum half-life and biological activity, and in part to the dimeric structure itself. The omission of lysine residues, such as at $X_{10}$ and $X'_{10}$, is also advantageous in that N-terminal specific modification is facilitated, i.e., no other amino groups are present in the peptide chains.

When the linker $L_K$ is lysine amide and n1 and n2 are zero, the dimer may be illustrated structurally as follows:

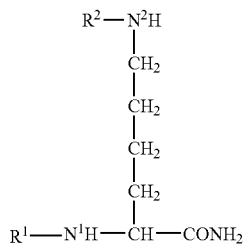
(II)

In formula (II), $N^2$ represents the nitrogen atom of lysine's ε-amino group and $N^1$ represents the nitrogen atom of lysine's α-amino group.

Similarly, when $L_K$ is lysine amide and n1 and n2 are both 1, the dimer has the structure of formula (III)

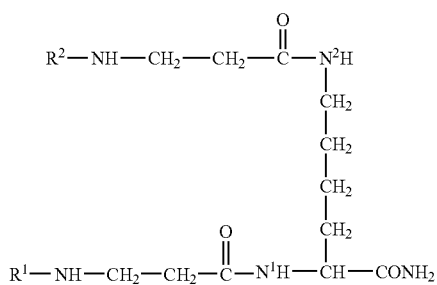
(III)

Analogously, structure (IV) represents a dimer herein wherein $L_K$ is lysine amide, n1 is zero and n2 is 1, while structure (V) represents a dimer wherein LK is lysine amide, n1 is 1 and n2 is zero:

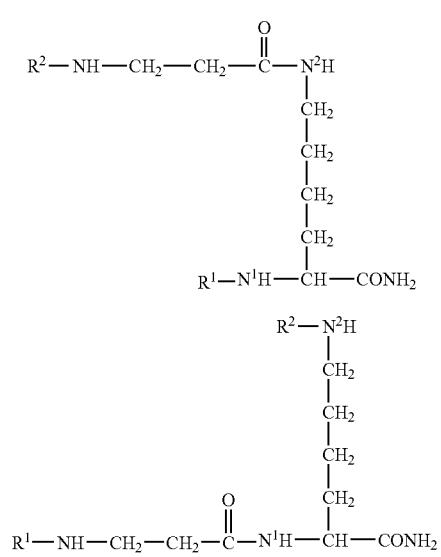
(IV)
(V)

Examples of particularly preferred $R^1$ and $R^2$ sequences include, but are not limited to, the following:

| | |
|---|---|
| GGTYSCHFGPLTBVCRPQGG; | (SEQ ID NO: 7) |
| GGTYSCHFGPLTBVCRPQGGK; | (SEQ ID NO: 8) |
| GGTYSCHFGPLTBVCRPQ; | (SEQ ID NO: 9) |
| GTYSCHFGPLTBVCRPQ; and | (SEQ ID NO: 10) |
| GGTYSCHFGPLTBVCJPQGG. | (SEQ ID NO: 11) |

Other preferred $R^1$ and $R^2$ sequences include, but are not limited to, the following:

| | |
|---|---|
| GGTYSCHFGPLTBVCQPLGG; | (SEQ ID NO: 12) |
| GGLYACHJGPJTBVCQPLRG; | (SEQ ID NO: 13) |
| GGLYACHMGPMTBVCQPLRG; | (SEQ ID NO: 14) |
| GGTYSCHFGPLTBVCRPQGG; | (SEQ ID NO: 15) |
| GGLYLCRFGPVTBDCGYKGG; | (SEQ ID NO: 16) |
| VGNYMCHFGPITBVCRPGGG; | (SEQ ID NO: 17) |
| GGVYACRMGPITBVCSPLGG; | (SEQ ID NO: 18) |
| GGPHHVYACRMGPLTBIC; | (SEQ ID NO: 19) |
| TIAQYICYMGPETBECRPSPKA; and | (SEQ ID NO: 20) |
| YCHFGPLTBVC. | (SEQ ID NO: 21) |

Numerous other sequences are also possible, however, including the following:

| | |
|---|---|
| YSCHFGPLTBVCK; | (SEQ ID NO: 22) |
| GGTYSCHFGPLTBVCKPQ | (SEQ ID NO: 23) |
| GGDYHCRMGPLTBVCKPLGG | (SEQ ID NO: 24) |
| GGTYSCHFGPLTBVCKPQGG | (SEQ ID NO: 25) |
| GGTYSCHFGPLTUVCRPQGG | (SEQ ID NO: 26) |
| GGTYRCSMGPMTBVCLPMGG; | (SEQ ID NO: 27) |
| GGMYSCRMGPMTBVCGPSGG; | (SEQ ID NO: 28) |
| GGWAWCRMGPITBVCSAHGG; | (SEQ ID NO: 29) |
| GGMYSCRMGPMTBVCIPYGG; | (SEQ ID NO: 30) |
| GGEYKCYMGPITBVCKPEGG; | (SEQ ID NO: 31) |
| GGDYTCRMGPMTBICTATGG; | (SEQ ID NO: 32) |
| GGNYLCRFGPGTBDCTGFRG; | (SEQ ID NO: 33) |
| GGNYVCRMGPITBICTPAGG; | (SEQ ID NO: 34) |
| GGKDVCRMGPITBDCRSTGG; | (SEQ ID NO: 35) |
| GGSYLCRMGPTTBLCTAQRGGGN; | (SEQ ID NO: 36) |
| GGNYLCRMGPATBVCGRMGG; | (SEQ ID NO: 37) |
| GGEYKCRMGPLTBVCQYAGG; | (SEQ ID NO: 38) |
| GGDYTCRMGPMTBICTATRG; | (SEQ ID NO: 39) |
| GGVYVCRMGPLTBECTASGG; | (SEQ ID NO: 40) |

-continued

| | |
|---|---|
| GGEYSCRMGPMTBVCSPTGG; | (SEQ ID NO: 41) |
| GGEYLCRMGPITBVCERYGG; | (SEQ ID NO: 42) |
| GGNYICRMGPMTBVCTAHGG; | (SEQ ID NO: 43) |
| GGDYLCRMGPATBVCGRMGG; | (SEQ ID NO: 44) |
| GGLYSCRMGPITBVCTKAGG; | (SEQ ID NO: 45) |
| GGGYHCRMGPMTBVCRPVGG; | (SEQ ID NO: 46) |
| GGIYKCLMGPLTBVCTPDGG; | (SEQ ID NO: 47) |
| GGLYSCLMGPITBLCKPKGG; | (SEQ ID NO: 48) |
| GGDYSCRMGPTTBVCTPPGG; | (SEQ ID NO: 49) |
| GGDYWCRMGPSTBECNAHGG; | (SEQ ID NO: 50) |
| GGKYLCSFGPITBVCARYGG; | (SEQ ID NO: 51) |
| GGLYKCRLGPITBVCSPLGG; | (SEQ ID NO: 52) |
| GGSYTCRFGPETBVCRPNGG; | (SEQ ID NO: 53) |
| GGSYSCRMGPITBVCKPGGG; | (SEQ ID NO: 54) |
| GGSYTCRMGPITBVCLPAGG; | (SEQ ID NO: 55) |
| GGLYECRMGPMTBVCRPGGG; | (SEQ ID NO: 56) |
| GGDYTCRMGPITBICTKAGG; | (SEQ ID NO: 57) |
| GGVYSCRMGPTTBECNRYVG; | (SEQ ID NO: 58) |
| GGAYLCHMGPITBVCRPQGG; | (SEQ ID NO: 59) |
| GGEYSCRMGPNTBVCKPVGG; | (SEQ ID NO: 60) |
| GGLYLCRMGPVTBECQPRGG; | (SEQ ID NO: 61) |
| GGLYTCRMGPITBVCLLPGG; | (SEQ ID NO: 62) |
| GGLYTCRMGPVTBVCTGAGG; | (SEQ ID NO: 63) |
| GGVYKCRMGPLTBECRPTGG; | (SEQ ID NO: 64) |
| GGDYNCRFGPLTBVCKPSGG; | (SEQ ID NO: 65) |
| GGSYLCRFGPTTBLCSSAGG; | (SEQ ID NO: 66) |
| GGSYLCRMGPTTBVCTRMGG; | (SEQ ID NO: 67) |
| GGSYLCRFGPTTBLCTQRGG; | (SEQ ID NO: 68) |
| GGWVTCRMGPITBVCGVHGG; | (SEQ ID NO: 69) |
| GGQLLCGIGPITBVCRWVGG; | (SEQ ID NO: 70) |
| GGKYSCFMGPTTBVCSPVGRGV; | (SEQ ID NO: 71) |
| GGWVYCRIGPITBVCDTNGG; | (SEQ ID NO: 72) |
| GGMYYCRMGPMTBVCKGAGG; | (SEQ ID NO: 73) |
| GGTTQCWIGPITBVCRARGG; | (SEQ ID NO: 74) |
| GGPYHCRMGPITBVCGPVGG; | (SEQ ID NO: 75) |
| GGEYRCRMGPISBVCSPQGG; | (SEQ ID NO: 76) |
| GGNYTCRFGPLTBECTPQGGGA; | (SEQ ID NO: 77) |
| GGSWDCRIGPITBVCKWSGG; | (SEQ ID NO: 78) |
| GGLYLCRMGPQTBMCQPGGG; | (SEQ ID NO: 79) |
| GGDYVCRMGPMTBVCAPYGR; | (SEQ ID NO: 80) |

-continued

| | |
|---|---|
| GGWYSCLMGPMTBVCKAHRG; | (SEQ ID NO: 81) |
| GGKYYCWMGPMTBVCSPAGG; | (SEQ ID NO: 82) |
| GGYVMCRIGPITBVCDIPGG; | (SEQ ID NO: 83) |
| GSCLQCCIGPITBVCRHAGG; | (SEQ ID NO: 84) |
| GGNYFCRMGPITBVCQRSVG; | (SEQ ID NO: 85) |
| GGEYICRMGPLTBECKRTGG; | (SEQ ID NO: 86) |
| GGLYACRMGPITBVCKYMAG; | (SEQ ID NO: 87) |
| GGQYLCTFGPITBLCRGAGG; | (SEQ ID NO: 88) |
| GGYTTCRMGPITBVCSAHGG; | (SEQ ID NO: 89) |
| GGTYKCWMGPMTBVCRPVGG; | (SEQ ID NO: 90) |
| GGNYYCRFGPITFECHPTGG; | (SEQ ID NO: 91) |
| GGEYLCRMGPMTBVCTPVGG; and | (SEQ ID NO: 92) |
| GGLYTCRMGPITBVCLPAGG. | (SEQ ID NO: 93) |

III. Dimer Synthesis:

The compounds of the invention can be prepared in one of two ways. Both methods involve, initially, providing a linking molecule that may be any suitable compound having two functional groups capable of serving as initiation sites for peptide synthesis, and a third functional group attachable to a solid support. The linking molecule is typically a diamine having the structure $H_2N$—$R^3$—$NH_2$, where $R^3$ is lower ($C_{1-6}$) alkylene substituted with a functional group such as a carboxyl group that enables binding to another molecular moiety (e.g., as may be present on the surface of a solid support), and is optionally substituted with a lower alkyl group. Dimer synthesis can then proceed by: (A) first synthesizing peptide chain $R^1$, with the two cysteine or homocysteine residues at $X_3$ and $X_9$ protected with a first thiol protecting group, e.g., trityl (Trt), allyloxycarbonyl (Alloc), 1-(4,4-dimethyl-2,6-dioxocyclohex-1-ylidene)ethyl (Dde), or the like, then synthesizing the second peptide chain $R^2$, with the two cysteine or homocysteine residues at $X'_3$ and $X'_9$ protected with a second thiol protecting group, different from the first, e.g., acetamidomethyl (Acm), t-butyl (tBu), or the like, then removing the first protecting group and effecting cyclization via a disulfide bond within $R^1$, and, finally, removing the second protecting group and effecting cyclization via a disulfide bond within $R^2$; or (B) simultaneously synthesizing peptide chains $R^1$ and $R^2$, using a single protecting group for the four cysteine or homocysteine residues at $X_3$, $X_9$, $X'_3$ and $X'_9$, removing the protecting group, and conducting an oxidative folding step which preferentially results in a dimer having an intramolecular disulfide bond linking $X_3$ and $X_9$, in $R_1$, and a second intramolecular disulfide bond linking $X'_3$ and $X'_9$, in $R^2$. These two methods are described in further detail below.

A. Sequential Synthesis of $R^1$ and $R^2$ and Regioselective Oxidation:

In one method, then, the initial linking molecule is protected with two different, orthogonally removable amine protecting groups. The protected diamine may be, for example, a protected lysine molecule. The protected linking molecule is coupled to a solid support through a functional group, e.g., a carboxylic acid moiety as is present in lysine or an amide moiety as is present in lysine amide. One of the two amine protecting groups is removed, and the first peptide $R^1$ is synthesized using the unprotected amine moiety as a starting point. The cysteine or homocysteine residues present at $X_3$ and $X_9$ are protected with a thiol protecting group, which is introduced by incorporation of the corresponding thiol protected amino acid during synthesis of the peptide chain. The remaining amine protecting group on the support-bound linking molecule is then removed, and the second peptide $R^2$ is synthesized using that unprotected amine moiety as a starting point. As with $R^1$, the cysteine or homocysteine residues present at $X'_3$ and $X'_9$ are protected with a thiol protecting group.

Standard solid phase peptide synthesis techniques are preferred for synthesis of $R^1$ and $R^2$, as described, for example, by Merrifield (1963) *J. Am. Chem. Soc.* 85:2149. As is well known in the art, solid phase synthesis using the Merrifield method involves successive coupling of α-amino protected amino acids to a growing support-bound peptide chain. After the initial coupling of a protected amino acid to a resin support (e.g., a polystyrene resin, a chloromethylated resin, a hydroxymethyl resin, a benzhydrylamine resin, or the like, depending on the chemistry used), the α-amino protecting group is removed by a choice of reagents, depending on the specific protecting group. Suitable α-amino protecting groups are those known to be useful in the art of stepwise synthesis of peptides. Included are acyl type protecting groups (e.g., formyl, trifluoroacetyl, acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, cyclohexyloxycarbonyl), alkyl type protecting groups (e.g., benzyl, triphenylmethyl), fluorenylmethyl oxycarbonyl (Fmoc), Alloc and Dde. The side chain protecting groups (typically ethers, esters, trityl, and the like) remain intact during coupling; however, the side chain protecting group must be removable upon completion of the synthesis of the final peptide. Preferred side chain protecting groups, as will appreciated by those skilled in the art, will depend on the particular amino acid that is being protected as well as the overall chemistry used. After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3 tetramethyluronium hexafluorophosphate (HBTU) or dicyclohexylcarbodiimide (DCC) in solution, for example, in methylene chloride ($CH_2Cl_2$), N-methyl pyrrolidone, dimethyl formamide (DMF), or mixtures thereof.

To protect cysteine and homocysteine residues during synthesis of the peptide chains $R^1$ and $R^2$, protecting groups are covalently linked to the free thiol moieties during synthesis, as noted above. Orthogonal protection, where different protecting groups are used to protect thiol moieties on the different dimer chains, allows cyclization within a chain without cross-reactions between chains. This is preferable, insofar as dimers containing disulfide bonds linking $R^1$ and $R^2$ are substantially less active than dimers in which each of $R^1$ and $R^2$ contain a cyclic group linking the two cysteine or homocysteine residues at $X_3$ and $X_9$ and at $X'_3$ and $X'_9$, respectively. Following synthesis of $R^1$ and $R^2$, then, the first thiol protecting group (e.g., protecting the two cysteine or homocysteine residues in $R^1$) is removed, and intramolecular cyclization is effected within $R^1$ using an oxidizing reagent suitable for forming disulfide bonds from free thiols. This step, accordingly, results in covalent binding of $X_3$ to $X_9$ through a disulfide bond. The second thiol protecting group is then removed (protecting the two cysteine or homocysteine residues in $R^2$), and intramolecular cyclization is effected in the second peptide chain, $R^2$, a similar manner. In this way, the dimer that is synthesized has a cyclic moiety in each of the two peptide chains, and disulfide bridges between the two peptide chains are not formed. As noted earlier herein, dimers in which each peptide chain contains a cyclic group are far more active than dimers in which the peptide chains are bridged through disulfide linkages, and it is thus highly preferable to optimize synthesis of the former dimer types.

After dimer synthesis is complete, the compound is cleaved from the solid support by treatment with a reagent such as trifluoroacetic acid, preferably in combination with a scavenger such as ethanedithiol, β-mercaptoethanol or thioanisole. The cleavage reagent not only cleaves the peptide from the resin, but also cleaves all remaining side chain protecting groups.

The above-described synthesis is a "regioselective" oxidation process in which orthogonally removable protecting groups are used for both amine protection of the support-bound linker and thiol protection within the newly synthesized peptide chains.

The synthesis is illustrated schematically in FIG. 2. In the figure, the linking moiety $L_K$ is an initial support-bound lysine residue. The lysine residue is shown as having a first amine protecting group, Alloc, protecting the ε-amino moiety, and a second protecting group, Fmoc, bound through a β-alanine residue ("βA") to the α-amino moiety. Other amine protecting moieties may of course be used, and as noted earlier herein the β-alanine residues are optional. The initial step of the synthesis involves removal of the Fmoc group using a suitable reagent, usually mild base (e.g., 20% piperidine in DMF), and the free amine group that results is then used as the starting point for the synthesis of a first peptide chain. The N-terminus of the completed chain is shown protected with Boc. The first peptide chain contains two thiol residues at $X_3$ and $X_9$, which are protected with a first protecting group $P^1$; these protecting groups are introduced during peptide synthesis by coupling thiol protected amino acids, i.e., cysteine or homocysteine in which the thiol moieties are protected with $P^1$. The second amine protecting group, the Alloc moiety, is then removed with a suitable reagent (e.g., $Pd(PPh_3)$/4-methyl morpholine and chloroform), and the free amine group that results is then used as the starting point for the synthesis of a second peptide chain. Like the first peptide chain, the second peptide chain contains two thiol residues, one at $X'_3$ and the other at $X'_9$. As may be seen in the figure, the two thiol residues in the second peptide chain are protected with a second protecting group $P^2$ (and, as for the first peptide chain, these protecting groups are introduced during synthesis of the peptide chain). The first thiol protecting group $P^1$ is removed, and, simultaneously, the terminal amine protecting group (Boc) is removed, side chain protecting groups are removed, and the dimer is cleaved from the support. Intramolecular cyclization is then effected within the first peptide chain using a suitable oxidizing reagent, e.g., aqueous dimethyl sulfoxide (DMSO). The second thiol protecting group, $P^2$, is then removed, and intramolecular cyclization is effected within the second peptide chain, again using a suitable oxidizing reagent. Optimally, removal of the second thiol protecting group and intramolecular cyclization in the second peptide chain are effected simultaneously using, for example, iodine/methanol (preferably in combination with thallium trifluoroacetate), trifluoroacetic acid/trimethylsilane, or the like.

B. Simultaneous Synthesis of $R^1$ and $R^2$ and Oxidative Folding:

A much preferred method involves an oxidative folding technique wherein orthogonally removable protecting groups are unnecessary and the overall number of reaction steps is reduced. In addition, when $R^1$ and $R^2$ are identical, as is the case in the preferred dimer compounds herein, the two peptide chains can be synthesized simultaneously.

In this method, then, the linking molecule is coupled to the solid support, as above, and synthesis of the two peptide chains of the dimer is carried out simultaneously using, for example, the Merrifield method as summarized in the preceding section. Protection of thiol groups in cysteine and homocysteine residues using two different protecting groups, as required in the synthesis described in Section A, is unnecessary. After synthesis of $R^1$ and $R^2$ is complete, the dimer—having free cysteine and/or homocysteine moieties in each peptide chain, at $X_3$, $X_9$, $X'_3$ and $X'_9$—is treated with an oxidizing composition effective to bring about intramolecular cyclization within each of the two peptide chains $R^1$ and $R^2$ while minimizing the formation of disulfide bridges therebetween. Generally, the oxidizing composition is an aqueous solution of an oxidizing reagent that is of a type and present at a concentration effective to optimize formation of the desired isomer, wherein each peptide chain contains a cyclic group formed by covalent bonding of $X_3$ to $X_9$, and $X'_3$ to $X'_9$, through a disulfide linkage. A particularly preferred oxidizing reagent is dimethyl sulfoxide, preferably in water at a concentration of about 15% to 100% (v/v), more preferably in the range of about 50% to 100% (v/v), and still more preferably in the range of 80% to 100% (v/v); most preferably the oxidizing composition comprises 100% DMSO. The cyclization reaction is conducted most advantageously at a temperature in the range of 5° C. to 30° C. for at least about 30 minutes, preferably at least about several hours, most preferably at least about 24 hours, and optimally for about 2 days.

Figure 3:
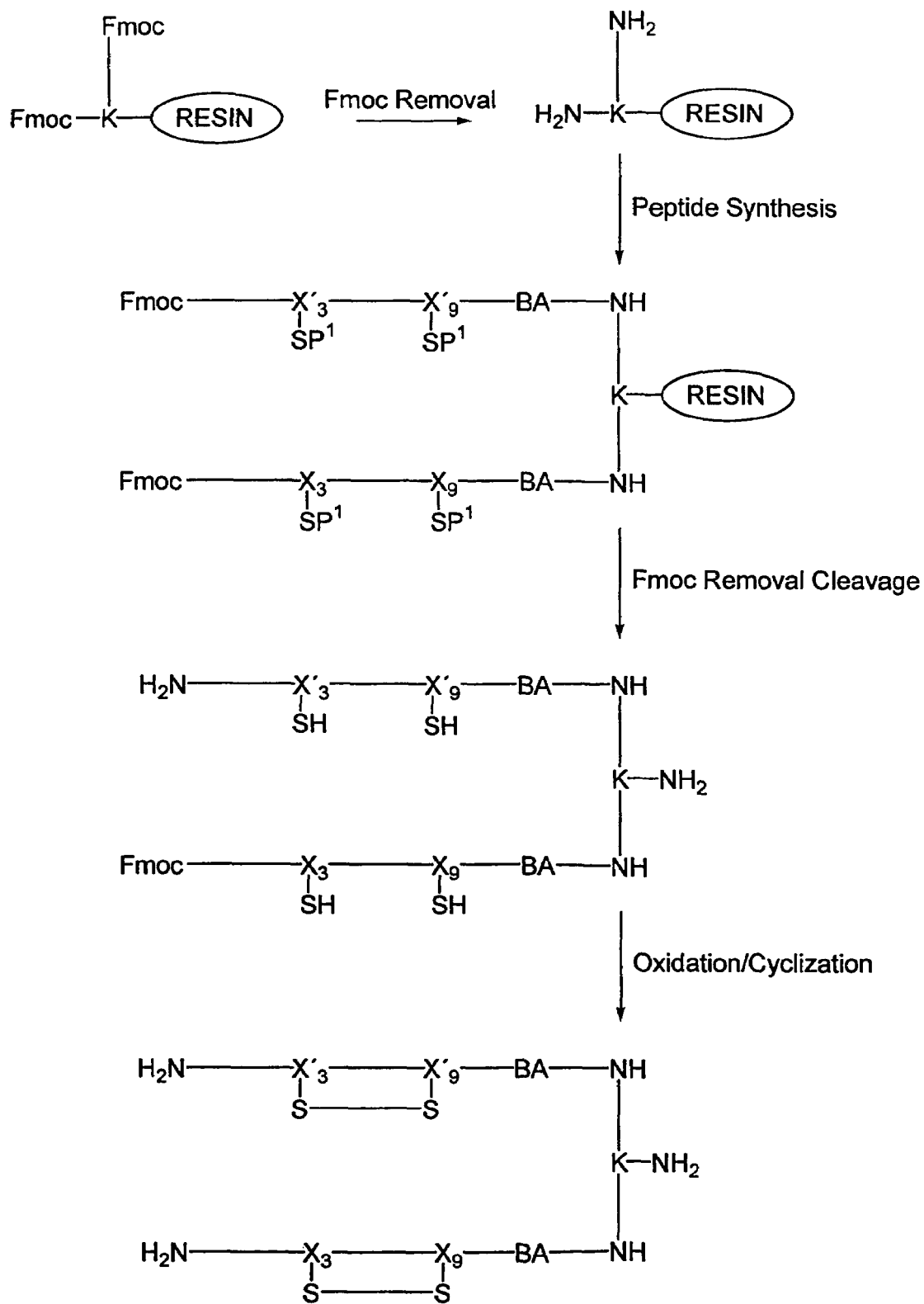

This synthetic method is illustrated schematically in FIG. 3. In FIG. 3, the initial support-bound lysine residue is shown as having two identical amine protecting groups (Fmoc groups in the figure, for purposes of illustration) protecting the α- and ε-amino moieties. The Fmoc groups are removed with a suitable reagent, and two free amine groups result. The two peptide chains are synthesized at each of the two free amine groups, simultaneously, using a single thiol protecting group $P^1$ for the cysteine and/or homocysteine residues. Following synthesis of the peptide chains, the dimer is cleaved from the solid support and subjected to oxidation using the oxidative folding technique just described. The desired isomer, in which a cyclic group is present in each of the two peptide chains (a disulfide bond links $X_3$ and $X_9$ in the first peptide chain, and a second disulfide bond links $X'_3$ and $X'_9$ in the second peptide chain), predominates.

Figure 4:
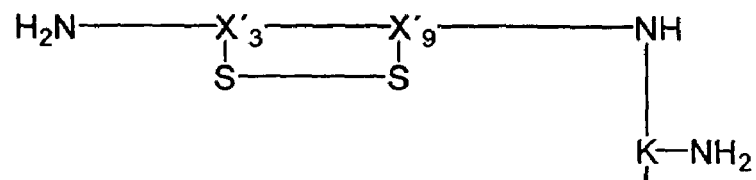
FIG. 4 illustrates the molecular structures of the three isomers that can result from dimer oxidation in the absence of a regioselective process.
Figure 4:
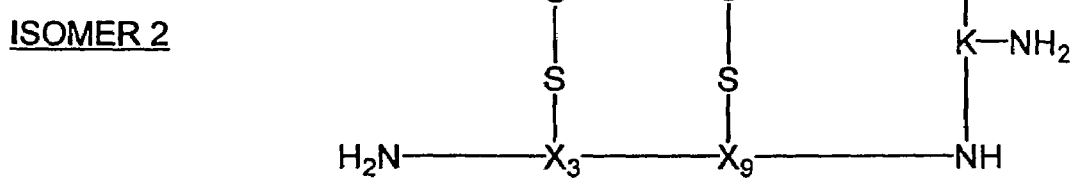
Figure 4:
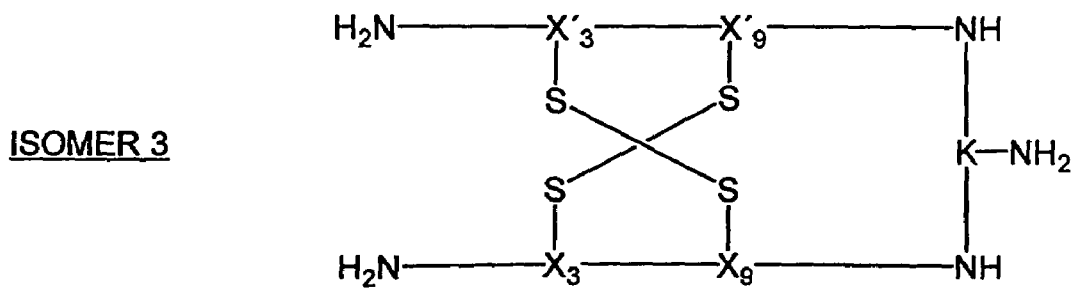
Figure 5:
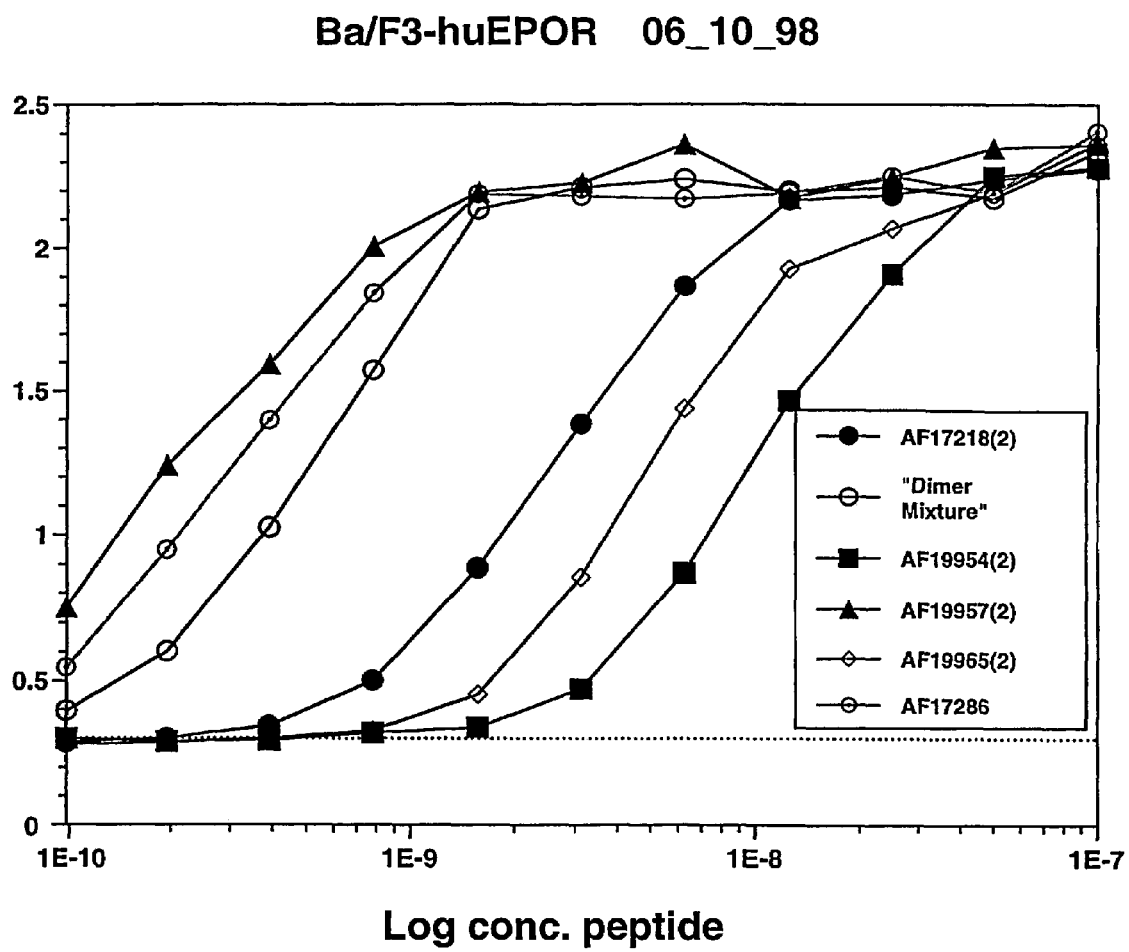
FIG. 5 illustrates the biological activity of various dimeric peptide analogs of the invention, as explained in Example 14.

In FIG. 4, the three isomers that can result from a one-step oxidative folding reaction are illustrated. Isomer 1 is far preferred, insofar as it is a substantially more active EPO agonist than either Isomer 2 or Isomer 3 (see FIG. 5, illustrating in graph form the comparative results vis-à-vis the individual isomers, as explained in Example 14). The aforementioned oxidative folding reaction preferentially gives rise to the desired compound, Isomer 1.

C. Dimer Synthesis—Variations and Further Modifications:

The procedures of parts (A) and (B) can also be used to synthesize dimers containing amino acids other than the 20 naturally occurring, genetically encoded amino acids. For instance, naphthylalanine can be substituted for tryptophan, with 1-naphthylalanine particularly preferred at $X_7$ and $X'_7$, facilitating synthesis and significantly improving activity. Other synthetic amino acids that can be substituted into the peptides of the present invention include, but are not limited to, nor-leucine and 3-pyridylalanine.

One can also modify the amino termini of the peptide chains of the dimer to produce other compounds of the invention. Amino terminus modifications include methylation (i.e., conversion of a free amino group to an —NHCH$_3$ or —N(CH$_3$)$_2$ moiety), acetylation (with either acetic acid per se, or with a halogenated derivative thereof such as α-chloroacetic acid, α-bromoacetic acid, or α-iodoacetic acid), addition of a benzyloxycarbonyl group, or blocking with a blocking group containing a carboxylate functionality RCOO— or a sulfonyl functionality R—SO$_2$—, where R is selected from the group consisting of alkyl, aryl, heteroaryl, alkyl aryl, and the like, and similar groups. One can also incorporate a desamino residue at the N-terminus, so that there is no terminal amino group, to decrease susceptibility to proteases or to restrict the conformation of the peptide chain or chains. Particularly preferred modifications herein, as explained in Section (II), are wherein the amino termini of both $R^1$ and $R^2$ are acetylated or conjugated to a polyethylene glycol molecule, with the latter modification most preferred. When N-terminal modification is desired, it is also preferred that the peptide chains contain no amino groups other than at the N-termini (and thus no lysine residues), so that N-terminal-specific modification may be carried out.

One can also replace the naturally occurring side chains of the 20 genetically encoded amino acids (or the stereoisomeric D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and 4-, 5-, 6-, to 7-membered heterocyclic. In particular, proline analogues in which the ring size of the proline residue is changed from 5 members to 4, 6, or 7 members can be employed.

One can also readily modify the peptide dimers herein by phosphorylation or other methods as described in Hruby et al., 1 Jun. 1990, *Biochem J.* 268:249-262. Thus, the peptide dimers of the invention also serve as structural models for non-peptidic compounds with similar biological activity. For example, the peptide backbones may be replaced with a backbone composed of phosphonates, amidates, carbamates, sulfonamides, secondary amines, and N-methylamino acids.

IV. Utility

The compounds of the invention are useful in vitro as unique tools for understanding the biological role of EPO, including the evaluation of the many factors thought to influence, and be influenced by, the production of EPO and the binding of EPO to the EPO-R (e.g., the mechanism of EPO signal transduction/receptor activation). The present compounds are also useful in the development of other compounds that bind to the EPO-R, because the present compounds provide important structure-activity relationship (SAR) information that facilitate that development.

Moreover, based on their ability to bind to the EPO receptor, the compounds of the present invention can be used as reagents for detecting EPO receptors on living cells, fixed cells, in biological fluids, in tissue homogenates, in purified, natural biological materials, etc. For example, by labeling such peptides, one can identify cells having EPO-R on their surfaces. In addition, based on their ability to bind the EPO receptor, the peptide dimers of the present invention can be used in in situ staining, FACS (fluorescence-activated cell sorting), Western blotting, ELISA (enzyme-linked immunoadsorptive assay), etc. In addition, based on their ability to bind to the EPO receptor, the peptide dimers of the present invention can be used in receptor purification or in purifying cells expressing EPO receptors on the cell surface (or inside permeabilized cells).

The compounds of the invention can also be utilized as commercial research reagents for various medical research and diagnostic uses. Such uses can include but are not limited to: (1) use as a calibration standard for quantitating the activities of candidate EPO agonists in a variety of functional assays; (2) use as blocking reagents in random peptide screening, i.e., in looking for new families of EPO receptor peptide ligands, the peptides can be used to block recovery of the presently claimed EPO peptides; (3) use in the co-crystallization with EPO receptor, i.e., the eptide dimers of the present invention will allow formation of crystals bound to the EPO receptor, enabling the determination of receptor/peptide structure x-ray crystallography; (4) use to measure the capacity of erythrocyte precursor cells to differentiate and thus stimulate the induction of globin synthesis and increases in the synthesis of the heme complex and in the number of ferritin receptors; (5) use to maintain the proliferation and growth of EPO-dependent cell lines, such as the FDCP-1-mEPO-R and the TF-1 cell lines; and (6) other research and diagnostic applications wherein the EPO-receptor is preferably activated or such activation is conveniently calibrated against a known quantity of an EPO agonist, and the like.

The compounds of the invention can also be administered to warm blooded animals, including humans, to simulate the binding of EPO to the EPO-R in vivo. Thus, the present invention encompasses methods for therapeutic treatment of disorders associated with a deficiency of EPO that comprise administering a compound of the invention in amounts sufficient to stimulate the EPO-R and thus alleviate the symptoms associated with a deficiency of EPO in vivo. For example, the compounds of this invention will find use in the treatment of end-stage renal failure/dialysis; anemia associated with AIDS, anemia associated with chronic inflammatory diseases (for example, rheumatoid arthritis and chronic bowel inflammation), autoimmune disease, and malignancies; and for boosting the red blood count of a patient prior to surgery.

Other embodiments of this invention provide for the administration of the compounds of the invention for the treatment of disorders which are not characterized by low or deficient red blood cells, for example as a pretreatment prior to transfusions. In addition, administration of the compounds of this invention can result in a decrease in bleeding time and thus will find use in the administration to patients prior to surgery or for indications wherein bleeding is expected to occur. In addition, the compounds of this invention will find use in the activation of megakaryoctes.

Since EPO has been shown to have a mitogenic and chemotactic effect on vascular endothelial cells as well as an effect on central cholinergic neurons (see, e.g., Amagnostou et al. (1990) *Proc. Natl. Acad. Sci. USA* 87:5978-5982 and Konishi et al. (1993) *Brain Res.* 609:29-35), the compounds of this invention will also find use for the treatment of a variety of vascular disorders, such as promoting wound healing, growth of collateral coronary blood vessels (such as those that may occur after myocardial infarction), trauma, and post-vascular graft treatment, and a variety of neurological disorders, generally characterized by low absolute levels of acetyl choline or low relative levels of acetyl choline as compared to other neuroactive substances e.g., neurotransmitters.

Accordingly, the present invention includes pharmaceutical compositions comprising, as an active ingredient, at least one of the peptide dimers of the invention in association with a pharmaceutical carrier or diluent. The compounds of this invention can be administered by oral, parenteral (intramuscular, intraperitoneal, intravenous (IV) or subcutaneous) injection, transdermal (either passively or using iontophoresis or electroporation), or transmucosal (nasal, vaginal, rectal, or sublingual) routes of administration, or using bioerodible inserts, and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally, dosage levels of between 0.001 to 10 mg/kg of body weight daily are administered to mammals.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entirety.

Experimental

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

The resin used (PAL) was obtained commercially available from Milligen/Biosearch. Solid phase reactions were carried out at room temperature. Unless otherwise indicated, all starting materials and reagents were obtained commercially, e.g., from Aldrich, Sigma and ICN, and used without further purification.

Also, in these examples and throughout this specification, the abbreviations employed have their generally accepted meanings, as follows:
Acm=acetamidomethyl
Alloc=allyloxycarbonyl
Boc=t-butoxycarbonyl
Bz=benzyl
Cbz=benzyloxycarbonyl
DMF=dimethyl formamide
Fmoc=fluorenylmethyl oxycarbonyl
g=gram
HBTU=O-(benzotriazol-1-yl)-1,1,3,3-tetramethyluronium hexafluorophosphate
HOBt=1-hydroxybenztriazole
ml=milliliter
mmol=millimole
MMT=monomethoxytrityl
Mts=mesitoylsulfonyl
Pmc=2,2,5,7,8-pentamethylchroman sulfonate
tBu=t-butyl
Tos=tosyl
Trt=trityl

EXAMPLE 1

Dimer Synthesis—Sequential Synthesis of the Individual Peptide Chains:

A dimeric compound of the invention was synthesized, the compound comprising two identical peptide chains having the sequence GGTYSCHFGPLTBVCRPQGG (SEQ ID NO: 7), wherein each peptide chain is linked at its carboxyl terminus to a lysine (K) amide linking group, with the two cysteine residues in the first peptide chain linked to each other through a disulfide bond, and, similarly, the two cysteine residues in the second peptide chain linked to each other through a disulfide bond. Initially, Fmoc-Lys-Alloc was coupled to PAL resin (Milligen/Biosearch), a cross-linked polystyrene, thereby providing an initial lysine residue to serve as the linker between the two chains to be synthesized. The Fmoc protecting group was removed with mild base (20% piperidine in DMF). The first peptide chain was then synthesized using the resulting free amino group, the α-$NH_2$ group, as a starting point. Peptide synthesis was conducted using the Merrifield solid phase synthesis technique (see, Stewart, J. M., and Young, J. D., *Solid Phase Peptide Synthesis*, 2d. edition (Pierce Chemical, Rockford, Ill., 1984)) on an Applied Biosystems 433A automated instrument. Primary amine protection on amino acids was achieved with Fmoc, and side chain protecting groups were tBu for serine, threosine and tyrosine, Trt for glutamine and asparagine, and Pmc for the arginine guanidino group. The two cysteine residues in the first peptide chain were protected with Trt. Each coupling was performed for either one or two hours with HBTU and HOBt.

Following synthesis of the first peptide chain, the Alloc group was removed from the support-bound lysine linker with Pd[P($C_6H_5$)$_3$]$_4$, 4-methyl morpholine and chloroform to allow synthesis of the second peptide chain (to remove Dde, 2% $NH_2$—$NH_2$ in DMF may be used). The second peptide chain was then synthesized on the ε-$NH_2$ group using the techniques described above, with Trt again used to protect the two cysteine residues.

After synthesis of the second peptide chain was complete, the dimer was cleaved from the PAL support with a mixture of 90% trifluoroacetic acid, 5% ethanedithiol, and 5% water, initially at 4° C., and gradually increasing to room temperature over 1.5 hours; the trifluoroacetic acid also removed all trityl protecting groups in both of the peptide chains. The deprotected product was filtered from the resin and precipitated with diethyl ether. After thorough drying the product was purified by C18 reverse phase high performance liquid chromatography with a gradient of acetonitrile/water in 0.1% trifluoroacetic acid. The resulting dimer has four free thiol groups, with two in each peptide chain. The identity of the product was confirmed by ESMS. The final yield was approximately 5% based on the initial loading of the resin.

EXAMPLES 2-5

The procedures of Example 1 were repeated to provide a number of additional dimers, set forth in Table 1. In the table, $L_K$, $R^1$, $R^2$, n1 and n2 are defined according to structural formula (I)

(I)

TABLE 1

PEPTIDE DIMERS WITH FREE CYSTEINE THIOLS

| Example No. | SEQ ID NO: | $R^1$ and $R^2$ | n1 | n2 | Linker | Code No. |
|---|---|---|---|---|---|---|
| (1) | 7 | GGTYSCHFGPLTBVCRPQGG | 0 | 0 | lysine | 17218 |
| 2 | 7 | GGTYSCHFGPLTBVCRPQGG | 1 | 0 | lysine | 20528 |
| 3 | 7 | GGTYSCHFGPLTBVCRPQGG | 1 | 1 | lysine | 20526 |
| 4 | 9 | GGTYSCHFGPLTBVCRPQ | 0 | 0 | lysine | 20532 |
| 5 | 10 | GTYSCHFGPLTBVCRPQ | 0 | 0 | lysine | 20531 |

EXAMPLE 6

Regioselective Oxidation:

A peptide dimer was synthesized as in Example 1, except that (1) cysteine residues in the second peptide chain were protected with Acm rather than Trt, and (2) following removal of the Trt protecting groups, the Acm groups were allowed to remain in place to enable regioselective oxidation. That is, an initial disulfide linkage, in the first peptide chain, was formed by (1) removing the Trt protecting groups using trifluoroacetic acid, followed by (2) stirring in 20% DMSO/water overnight. The Acm protecting groups in the second peptide chain were then removed by treatment with iodine/methanol and thallium trifluoroacetate, which also oxidized the second peptide chain to form a second intramolecular cyclic group. The preferred isomer was obtained in high yield.

EXAMPLES 7-9

The procedures of Example 6 were repeated to provide a number of additional dimers, set forth in Table 2; like the compound prepared in Example 6, each of these dimers contained an intramolecular cyclic group in the first peptide chain (formed via a disulfide bridge between the two cysteine residues), and a second intramolecular cyclic group in the second peptide chain (again, formed via a disulfide bridge between the two cysteine residues). In the table, $L_K$, $R^1$, $R^2$, n1 and n2 are defined according to structural formula (I), above.

TABLE 2

PEPTIDE DIMERS WITH AN INTRAMOLECULAR CYCLIC GROUP IN EACH PEPTIDE CHAIN

| Example No. | SEQ ID NO: | $R^1$ and $R^2$ | n1 | n2 | Linker | Code No. |
|---|---|---|---|---|---|---|
| (6) | 7 | GGTYSCHFGPLTBVCRPQGG | 0 | 0 | lysine | 19957 |
| 7 | 7 | GGTYSCHFGPLTBVCRPQGG | 1 | 0 | lysine | 17286 |
| 8 | 7 | GGTYSCHFGPLTBVCRPQGG | 1 | 1 | lysine | 19261 |
| 9 | 11 | GGTYSCHFGPLTBVCJPQGG | 1 | 0 | lysine | 17393 |

EXAMPLES 10-12

Amino Terminus Modification:

It will be appreciated by those skilled in the art that one can also modify the amino terminus of the first and/or second peptide chains within the compounds of the invention to produce additional compounds of the invention. Particularly preferred modifications involve (1) acetylation of the two amino termini of the dimer, and (2) "PEGylation" of the two amino termini of the dimer, i.e., covalent attachment of polyethylene glycol moieties.

The modified dimer compounds prepared are set forth in Table 3:

TABLE 3

PEPTIDE DIMERS MODIFIED AT THE N-TERMINUS OF EACH PEPTIDE CHAIN

| Example No. | SEQ ID NO: | $R^1$ and $R^2$, end modifier | n1 | n2 | Linker | Code No. |
|---|---|---|---|---|---|---|
| 10 | 7 | GGTYSCHFGPLTBVCRPQGG, both N-termini acetylated | 1 | 0 | lysine | 17644 |
| 11 | 7 | GGTYSCHFGPLTBVCRPQGG, both N-termini PEGylated | 1 | 1 | lysine | 17762 |
| 12 | 8 | GGTYSCHFGPLTBVCRPQGGK both N-termini acetylated | 0 | 0 | =O | 20952 |

EXAMPLE 13

Oxidative Folding:

The peptide dimer of Example 6 was synthesized using an alternative technique in which the two peptide chains were synthesized simultaneously (in contrast to the successive synthesis set forth in Example 1) and intramolecular cyclization between cysteine residues in each peptide chain was obtained by a single oxidative step (rather than by a multi-step regioselective process as described in Example 6).

Fmoc-Lys-Fmoc was coupled to PAL resin (Milligen/Biosearch), thereby providing an initial lysine residue to serve as the linker between the two chains to be synthesized. The Fmoc protecting groups were removed with mild base (20% piperidine in DMF), and the peptide chains were then synthesized using the resulting free amino groups as starting points. As in Example 1, peptide synthesis was conducted using Merrifield solid phase synthesis on an Applied Biosystems 433A automated instrument. Primary amine protection on amino acids was achieved with Fmoc, and side chain protecting groups were t-butyl for serine, threonine and tyrosine, trityl for glutamine and asparagine, and Pmc for the arginine guanidino group; Trt was used to protect all cysteine residues. After synthesis of the peptide, the dimer was cleaved from the PAL support with a mixture of 90% trifluoroacetic acid, 5% ethanedithiol, and 5% water, as in Example 1. The deprotected product was filtered from the resin and precipitated with diethyl ether. After thorough drying the product was purified by C18 reverse phase high performance liquid chromatography with a gradient of acetonitrile/water in 0.1% trifluoroacetic acid.

Oxidation of the cysteine residues can produce three different isomers of the peptide dimer, as illustrated in FIG. 4: (1) Isomer 1, wherein each peptide chain contains a cyclic group formed by a disulfide linkage between cysteine residues within the chain; (2) Isomer 2, containing disulfide linkages between analogous cysteine residues on opposite monomer chains; and (3) Isomer 3, containing disulfide linkages between nonanalogous cysteines on opposite monomers. Isomer 1 is far preferred, insofar as it is a substantially more active EPO agonist than either Isomer 2 or Isomer 3.

Thus, to oxidize the peptide dimer and link the cysteine residues in the preferred manner, the dimer (having all cysteine thiols unprotected), was incubated in an aqueous solution of DMSO (20% DMSO-80% water, v/v) at 5° C., 1 mg/ml, for several hours. All three isomers were obtained, with approximately 50% of the product comprising Isomer 1. The process was then repeated using an aqueous solution of DMSO with an increased DMSO concentration (50% DMSO-50% water, v/v). Again, all three isomers were obtained, with approximately 75% of the product comprising Isomer 1. The most preferred method, which yielded the largest fraction of the desired isomer, employed 100% DMSO (at a temperature between 5° C. and 25° C., with a reaction time of at least several hours, optimally 2 to 3 days).

EXAMPLE 14

Bioassay:

Peptide dimers of the invention were evaluated with respect to in vitro biological activity using an EPO receptor binding assay and a cell proliferation assay in which bioactivity was determined by Ba/F3-huEPOR cell proliferation. The protocol for each assay is described in Wrighton et al. (1997) *Nature Biotechnology* 15:1261-1265, and in U.S. Pat. Nos. 5,773,569 and 5,830,851, both to Wrighton et al. and cited earlier herein. $EC_{50}$ values for the dimers prepared in Examples 1-12 are set forth in Table 4 (the $EC_{50}$ value is the concentration of compound required to produce 50% of the maximal activity obtained with recombinant erythropoietin).

TABLE 4

BIOASSAY RESULTS

| Dimer-Example No. | Code | $EC_{50}$ (nM) |
|---|---|---|
| 1 | 17218 | 6 |
| 2 | 20528 | 6 |
| 3 | 20526 | 5 |
| 4 | 20532 | 50 |
| 5 | 20531 | 100 |
| 6 | 19957 | 0.5 |
| 7 | 17286 | 0.4 |
| 8 | 19261 | 0.3 |
| 9 | 17393 | 2 |
| 10 | 17644 | 5 |
| 11 | 17762 | 0.4 |
| 12 | 20952 | 2 |

The compounds of the invention are thus highly active EPO agonists. Their activity is significantly higher than the monomeric compounds; for example, a monomeric compound having the sequence GGTYSCHFGPLTBVCRPQGG (SEQ ID NO: 7), a compound previously viewed as a highly active EPO agonist (see U.S. Pat. No. 5,773,569 to Wrighton et al.), was determined to have an $EC_{50}$ of 200 nM using the above-described assay. In addition, both N-terminal PEGylation and replacement of lysine (K) with 1-naphthylalanine at $X_7$ and $X'_7$ were found to significantly increase potency.

With regard to the different isomers of the dimer prepared in Example 13 (see FIG. 4), i.e., Isomer 1 (Code No. 19957), Isomer 2 (Code No. 19954) and Isomer 3 (Code No. 19965), FIG. 5 illustrates that the in vitro bioactivity of Isomer 1 was noticeably higher than the measured in vitro bioactivity of any of the other compounds.

The invention claimed is:

1. A method for synthesizing a peptide dimer, comprising:
   (a) providing first and second peptide chains linked to a linking moiety $L_K$, said chains each possessing multiple amino acid residues capable of disulfide bond formation upon oxidation; and
   (b) oxidizing in a single oxidation step said peptide chains in a manner effective to preferentially promote formation of disulfide bonds between residues in the same peptide chain relative to formation of disulfide bonds in different peptide chains, and wherein at least 50% of said peptide dimer comprises a peptide chain having an intrapeptide disulfide bond.

2. The method of claim 1, wherein step (b) comprises treatment with an oxidizing composition containing an oxidizing reagent in an amount effective to minimize reaction products in which a residue of the first peptide chain binds to a residue of the second peptide chain.

3. The method of claim 2, wherein the oxidizing reagent is dimethyl sulfoxide.

4. The method of claim 3, wherein the oxidizing composition comprises approximately 15% to 100% (v/v) dimethyl sulfoxide.

5. The method of claim 4, wherein the oxidizing composition comprises approximately 50% to 100% (v/v) dimethyl sulfoxide.

6. The method of claim 5, wherein the oxidizing composition comprises approximately 80% to 100% (v/v) dimethyl sulfoxide.

7. The method of claim 6, wherein the oxidizing composition comprises approximately 100% (v/v) dimethyl sulfoxide.

8. The method of claim 1, wherein the first peptide chain is approximately 10 to 40 amino acid residues in length, binds to the erythropoietin receptor, and contains a sequence of amino acids X3X4X5GPX6TX7X8X9, wherein each amino acid is indicated by standard one-letter abbreviation, wherein X3 is C or homocysteine (Hoc), X4 is R, H, L or W, X5 is M, F, I or nor-leucine (J), X6 is selected from any one of the 20 conventional amino acids and J, X7 is W, 1-naphthylalanine (B) or 2-naphthylalanine (U), X8 is D, E, I, L, or V, and X9 is C or Hoc; and the second peptide chain is approximately 10 to 40 amino acid residues in length, binds to the erythropoietin receptor, and contains a sequence of amino acids X'3X'4X'5GPX'6TX'7X'8X'9, wherein each amino acid is indicated by standard one-letter abbreviation, wherein X'3 is C or Hoc, X'4 is R, H, L or W, X'5 is M, F, I or J, X'6 is selected from any one of the 20 conventional amino acids and J, X'7 is W, B or U, X'8 is D, E, I, L or V, and X'9 is C or Hoc.

9. The method of claim 8, wherein one or more of said amino acid residues are genetically coded L-amino acids.

10. The method of claim 8, wherein the amino terminus of at least one of said peptide chains is modified.

11. The method of claim 10, wherein at least one of said peptide chains comprises a non-naturally occurring amino acid residue.

12. The method of claim 1, wherein at least one of said peptide chains comprises an amino acid residue, wherein a naturally occurring side chain of said amino acid residue is replaced with a non-naturally occurring side chain.

13. The method of claim 1, wherein said first peptide chain binds to the erythropoietin receptor and wherein said second peptide chain binds to the erythropoietin receptor.

* * * * *

SEQUENCE LISTING

```
<160> NUMBER OF SEQ ID NOS: 93

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: C or Homocysteine
<220> FEATURE:
<221> NAME/KEY: MOD_RES
<222> LOCATION: (2)
<223> OTHER INFORMATION: R, H, L or W
<220> FEATURE:
<221> NAME/KEY: MOD_RES
<222> LOCATION: (3)
<223> OTHER INFORMATION: M, F, I or nor-leucine
<220> FEATURE:
<221> NAME/KEY: MOD_RES
<222> LOCATION: (6)
<223> OTHER INFORMATION: Any amino acid or nor-leucine
<220> FEATURE:
<221> NAME/KEY: MOD_RES
<222> LOCATION: (8)
<223> OTHER INFORMATION: W, 1-Nal or 2-Nal
<220> FEATURE:
<221> NAME/KEY: MOD_RES
<222> LOCATION: (9)
<223> OTHER INFORMATION: D, E, I, L or V
```

```
<220> FEATURE:
<221> NAME/KEY: MOD_RES
<222> LOCATION: (10)
<223> OTHER INFORMATION: C or Homocysteine

<400> SEQUENCE: 1

Xaa Xaa Xaa Gly Pro Xaa Thr Xaa Xaa Xaa
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: C or Homocysteine
<220> FEATURE:
<221> NAME/KEY: MOD_RES
<222> LOCATION: (2)
<223> OTHER INFORMATION: R, H, L or W
<220> FEATURE:
<221> NAME/KEY: MOD_RES
<222> LOCATION: (3)
<223> OTHER INFORMATION: M, F, I or nor-leucine
<220> FEATURE:
<221> NAME/KEY: MOD_RES
<222> LOCATION: (6)
<223> OTHER INFORMATION: Any amino acid or nor-leucine
<220> FEATURE:
<221> NAME/KEY: MOD_RES
<222> LOCATION: (8)
<223> OTHER INFORMATION: W, 1-Nal or 2-Nal
<220> FEATURE:
<221> NAME/KEY: MOD_RES
<222> LOCATION: (9)
<223> OTHER INFORMATION: D, E, I, L or V
<220> FEATURE:
<221> NAME/KEY: MOD_RES
<222> LOCATION: (10)
<223> OTHER INFORMATION: C or Homocysteine

<400> SEQUENCE: 2

Xaa Xaa Xaa Gly Pro Xaa Thr Xaa Xaa Xaa
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (3)
<223> OTHER INFORMATION: C or Homocysteine
<220> FEATURE:
<221> NAME/KEY: MOD_RES
<222> LOCATION: (4)
<223> OTHER INFORMATION: R, H or L
<220> FEATURE:
<221> NAME/KEY: MOD_RES
<222> LOCATION: (5)
<223> OTHER INFORMATION: M, F or I
<220> FEATURE:
<221> NAME/KEY: MOD_RES
<222> LOCATION: (8)
```

-continued

```
<223> OTHER INFORMATION: Any amino acid
<220> FEATURE:
<221> NAME/KEY: MOD_RES
<222> LOCATION: (10)
<223> OTHER INFORMATION: 1-Nal
<220> FEATURE:
<221> NAME/KEY: MOD_RES
<222> LOCATION: (11)
<223> OTHER INFORMATION: D, E, I, L or V
<220> FEATURE:
<221> NAME/KEY: MOD_RES
<222> LOCATION: (12)
<223> OTHER INFORMATION: C or Homocysteine
<220> FEATURE:
<221> NAME/KEY: MOD_RES
<222> LOCATION: (13)
<223> OTHER INFORMATION: Any amino acid

<400> SEQUENCE: 3

Tyr Xaa Xaa Xaa Xaa Gly Pro Xaa Thr Xaa Xaa Xaa Xaa
  1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (3)
<223> OTHER INFORMATION: C or Homocysteine
<220> FEATURE:
<221> NAME/KEY: MOD_RES
<222> LOCATION: (4)
<223> OTHER INFORMATION: R, H or L
<220> FEATURE:
<221> NAME/KEY: MOD_RES
<222> LOCATION: (5)
<223> OTHER INFORMATION: M, F or I
<220> FEATURE:
<221> NAME/KEY: MOD_RES
<222> LOCATION: (8)
<223> OTHER INFORMATION: Any amino acid
<220> FEATURE:
<221> NAME/KEY: MOD_RES
<222> LOCATION: (10)
<223> OTHER INFORMATION: 1-Nal
<220> FEATURE:
<221> NAME/KEY: MOD_RES
<222> LOCATION: (11)
<223> OTHER INFORMATION: D, E, I, L or V
<220> FEATURE:
<221> NAME/KEY: MOD_RES
<222> LOCATION: (12)
<223> OTHER INFORMATION: C or Homocysteine
<220> FEATURE:
<221> NAME/KEY: MOD_RES
<222> LOCATION: (13)
<223> OTHER INFORMATION: Any amino acid

<400> SEQUENCE: 4

Tyr Xaa Xaa Xaa Xaa Gly Pro Xaa Thr Xaa Xaa Xaa Xaa
  1               5                  10

<210> SEQ ID NO 5
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (5)
<223> OTHER INFORMATION: R or H
<220> FEATURE:
<221> NAME/KEY: MOD_RES
<222> LOCATION: (6)
<223> OTHER INFORMATION: M or F
<220> FEATURE:
<221> NAME/KEY: MOD_RES
<222> LOCATION: (9)
<223> OTHER INFORMATION: Any amino acid
<220> FEATURE:
<221> NAME/KEY: MOD_RES
<222> LOCATION: (11)
<223> OTHER INFORMATION: 1-Nal
<220> FEATURE:
<221> NAME/KEY: MOD_RES
<222> LOCATION: (12)
<223> OTHER INFORMATION: D, E, I, L or V
<220> FEATURE:
<221> NAME/KEY: MOD_RES
<222> LOCATION: (14)
<223> OTHER INFORMATION: R
<220> FEATURE:
<221> NAME/KEY: MOD_RES
<222> LOCATION: (15)..(16)
<223> OTHER INFORMATION: Any amino acid

<400> SEQUENCE: 5

Xaa Tyr Xaa Cys Xaa Xaa Gly Pro Xaa Thr Xaa Xaa Cys Xaa Xaa Xaa
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any amino acid
<220> FEATURE:
<221> NAME/KEY: MOD_RES
<222> LOCATION: (3)
<223> OTHER INFORMATION: Any amino acid
<220> FEATURE:
<221> NAME/KEY: MOD_RES
<222> LOCATION: (5)
<223> OTHER INFORMATION: R or H
<220> FEATURE:
<221> NAME/KEY: MOD_RES
<222> LOCATION: (6)
<223> OTHER INFORMATION: M or F
<220> FEATURE:
<221> NAME/KEY: MOD_RES
<222> LOCATION: (9)
<223> OTHER INFORMATION: Any amino acid
<220> FEATURE:
<221> NAME/KEY: MOD_RES
<222> LOCATION: (11)
<223> OTHER INFORMATION: 1-Nal
<220> FEATURE:
<221> NAME/KEY: MOD_RES
<222> LOCATION: (12)

```
<223> OTHER INFORMATION: D, E, I, L or V
<220> FEATURE:
<221> NAME/KEY: MOD_RES
<222> LOCATION: (14)
<223> OTHER INFORMATION: R
<220> FEATURE:
<221> NAME/KEY: MOD_RES
<222> LOCATION: (15)..(16)
<223> OTHER INFORMATION: Any amino acid

<400> SEQUENCE: 6

Xaa Tyr Xaa Cys Xaa Xaa Gly Pro Xaa Thr Xaa Xaa Cys Xaa Xaa Xaa
 1               5                  10                  15

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 7

Gly Gly Thr Tyr Ser Cys His Phe Gly Pro Leu Thr Xaa Val Cys Arg
 1               5                  10                  15

Pro Gln Gly Gly
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 8

Gly Gly Thr Tyr Ser Cys His Phe Gly Pro Leu Thr Xaa Val Cys Arg
 1               5                  10                  15

Pro Gln Gly Gly Lys
            20

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 9

Gly Gly Thr Tyr Ser Cys His Phe Gly Pro Leu Thr Xaa Val Cys Arg
 1               5                  10                  15

Pro Gln

<210> SEQ ID NO 10
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: 1-Nal

<400> SEQUENCE: 10

Gly Thr Tyr Ser Cys His Phe Gly Pro Leu Thr Xaa Val Cys Arg Pro
 1               5                  10                  15

Gln

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 11

Gly Gly Thr Tyr Ser Cys His Phe Gly Pro Leu Thr Xaa Val Cys Pro
 1               5                  10                  15

Gln Gly Gly

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 12

Gly Gly Thr Tyr Ser Cys His Phe Gly Pro Leu Thr Xaa Val Cys Gln
 1               5                  10                  15

Pro Leu Gly Gly
            20

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: 1-Nal

<400> SEQUENCE: 13

Gly Gly Leu Tyr Ala Cys His Gly Pro Thr Xaa Val Cys Gln Pro Leu
 1               5                  10                  15

Arg Gly
```

```
<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 14

Gly Gly Leu Tyr Ala Cys His Met Gly Pro Met Thr Xaa Val Cys Gln
 1               5                  10                  15

Pro Leu Arg Gly
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 15

Gly Gly Thr Tyr Ser Cys His Phe Gly Pro Leu Thr Xaa Val Cys Arg
 1               5                  10                  15

Pro Gln Gly Gly
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 16

Gly Gly Leu Tyr Leu Cys Arg Phe Gly Pro Val Thr Xaa Asp Cys Gly
 1               5                  10                  15

Tyr Lys Gly Gly
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 17

Val Gly Asn Tyr Met Cys His Phe Gly Pro Ile Thr Xaa Val Cys Arg
```

```
            1               5                  10                  15
Pro Gly Gly Gly
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 18

Gly Gly Val Tyr Ala Cys Arg Met Gly Pro Ile Thr Xaa Val Cys Ser
  1               5                  10                  15
Pro Leu Gly Gly
            20

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)
<223> OTHER INFORMATION: 1-Nal

<400> SEQUENCE: 19

Gly Gly Pro His His Val Tyr Ala Cys Arg Met Gly Pro Leu Thr Xaa
  1               5                  10                  15
Ile Cys

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: 1-Nal

<400> SEQUENCE: 20

Thr Ile Ala Gln Tyr Ile Cys Tyr Met Gly Pro Glu Thr Xaa Glu Cys
  1               5                  10                  15
Arg Pro Ser Pro Lys Ala
            20

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 1-Nal
```

```
<400> SEQUENCE: 21

Tyr Cys His Phe Gly Pro Leu Thr Xaa Val Cys
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: 1-Nal

<400> SEQUENCE: 22

Tyr Ser Cys His Phe Gly Pro Leu Thr Xaa Val Cys Lys
 1               5                  10

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 23

Gly Gly Thr Tyr Ser Cys His Phe Gly Pro Leu Thr Xaa Val Cys Lys
 1               5                  10                  15

Pro Gln

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 24

Gly Gly Asp Tyr His Cys Arg Met Gly Pro Leu Thr Xaa Val Cys Lys
 1               5                  10                  15

Pro Leu Gly Gly
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 25
```

```
Gly Gly Thr Tyr Ser Cys His Phe Gly Pro Leu Thr Xaa Val Cys Lys
  1               5                   10                  15

Pro Gln Gly Gly
            20

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Thr Tyr Ser Cys His Phe Gly Pro Leu Thr Val Cys Arg Pro
  1               5                   10                  15

Gln Gly Gly

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 27

Gly Gly Thr Tyr Arg Cys Ser Met Gly Pro Met Thr Xaa Val Cys Leu
  1               5                   10                  15

Pro Met Gly Gly
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 28

Gly Gly Met Tyr Ser Cys Arg Met Gly Pro Met Thr Xaa Val Cys Gly
  1               5                   10                  15

Pro Ser Gly Gly
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 29
```

```
Gly Gly Trp Ala Trp Cys Arg Met Gly Pro Ile Thr Xaa Val Cys Ser
 1               5                  10                  15

Ala His Gly Gly
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 30

Gly Gly Met Tyr Ser Cys Arg Met Gly Pro Met Thr Xaa Val Cys Ile
 1               5                  10                  15

Pro Tyr Gly Gly
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 31

Gly Gly Glu Tyr Lys Cys Tyr Met Gly Pro Ile Thr Xaa Val Cys Lys
 1               5                  10                  15

Pro Glu Gly Gly
            20

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 32

Gly Gly Asp Tyr Thr Cys Arg Met Gly Pro Met Thr Xaa Ile Cys Thr
 1               5                  10                  15

Ala Thr Gly Gly
            20

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (13)
<223> OTHER INFORMATION: 1-Nal

<400> SEQUENCE: 33

Gly Gly Asn Tyr Leu Cys Arg Phe Gly Pro Gly Thr Xaa Asp Cys Thr
 1               5                  10                  15

Gly Phe Arg Gly
            20

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 34

Gly Gly Asn Tyr Val Cys Arg Met Gly Pro Ile Thr Xaa Ile Cys Thr
 1               5                  10                  15

Pro Ala Gly Gly
            20

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 35

Gly Gly Lys Asp Val Cys Arg Met Gly Pro Ile Thr Xaa Asp Cys Arg
 1               5                  10                  15

Ser Thr Gly Gly
            20

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 36

Gly Gly Ser Tyr Leu Cys Arg Met Gly Pro Thr Thr Xaa Leu Cys Thr
 1               5                  10                  15

Ala Gln Arg Gly Gly Gly Asn
            20

<210> SEQ ID NO 37
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 37

Gly Gly Asn Tyr Leu Cys Arg Met Gly Pro Ala Thr Xaa Val Cys Gly
 1               5                  10                  15

Arg Met Gly Gly
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 38

Gly Gly Glu Tyr Lys Cys Arg Met Gly Pro Leu Thr Xaa Val Cys Gln
 1               5                  10                  15

Tyr Ala Gly Gly
            20

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 39

Gly Gly Asp Tyr Thr Cys Arg Met Gly Pro Met Thr Xaa Ile Cys Thr
 1               5                  10                  15

Ala Thr Arg Gly
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 40

Gly Gly Val Tyr Val Cys Arg Met Gly Pro Leu Thr Xaa Glu Cys Thr
 1               5                  10                  15

Ala Ser Gly Gly
            20
```

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 41

Gly Gly Glu Tyr Ser Cys Arg Met Gly Pro Met Thr Xaa Val Cys Ser
 1               5                  10                  15

Pro Thr Gly Gly
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 42

Gly Gly Glu Tyr Leu Cys Arg Met Gly Pro Ile Thr Xaa Val Cys Glu
 1               5                  10                  15

Arg Tyr Gly Gly
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 43

Gly Gly Asn Tyr Ile Cys Arg Met Gly Pro Met Thr Xaa Val Cys Thr
 1               5                  10                  15

Ala His Gly Gly
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 44

-continued

```
Gly Gly Asp Tyr Leu Cys Arg Met Gly Pro Ala Thr Xaa Val Cys Gly
 1               5                   10                  15

Arg Met Gly Gly
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 45

Gly Gly Leu Tyr Ser Cys Arg Met Gly Pro Ile Thr Xaa Val Cys Thr
 1               5                   10                  15

Lys Ala Gly Gly
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 46

Gly Gly Gly Tyr His Cys Arg Met Gly Pro Met Thr Xaa Val Cys Arg
 1               5                   10                  15

Pro Val Gly Gly
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 47

Gly Gly Ile Tyr Lys Cys Leu Met Gly Pro Leu Thr Xaa Val Cys Thr
 1               5                   10                  15

Pro Asp Gly Gly
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (13)
<223> OTHER INFORMATION: 1-Nal

<400> SEQUENCE: 48

Gly Gly Leu Tyr Ser Cys Leu Met Gly Pro Ile Thr Xaa Leu Cys Lys
 1               5                  10                  15

Pro Lys Gly Gly
         20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 49

Gly Gly Asp Tyr Ser Cys Arg Met Gly Pro Thr Thr Xaa Val Cys Thr
 1               5                  10                  15

Pro Pro Gly Gly
         20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 50

Gly Gly Asp Tyr Trp Cys Arg Met Gly Pro Ser Thr Xaa Glu Cys Asn
 1               5                  10                  15

Ala His Gly Gly
         20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 51

Gly Gly Lys Tyr Leu Cys Ser Phe Gly Pro Ile Thr Xaa Val Cys Ala
 1               5                  10                  15

Arg Tyr Gly Gly
         20

<210> SEQ ID NO 52
<211> LENGTH: 20
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 52

Gly Gly Leu Tyr Lys Cys Arg Leu Gly Pro Ile Thr Xaa Val Cys Ser
  1               5                  10                  15

Pro Leu Gly Gly
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 53

Gly Gly Ser Tyr Thr Cys Arg Phe Gly Pro Glu Thr Xaa Val Cys Arg
  1               5                  10                  15

Pro Asn Gly Gly
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 54

Gly Gly Ser Tyr Ser Cys Arg Met Gly Pro Ile Thr Xaa Val Cys Lys
  1               5                  10                  15

Pro Gly Gly Gly
            20

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 55

Gly Gly Ser Tyr Thr Cys Arg Met Gly Pro Ile Thr Xaa Val Cys Leu
  1               5                  10                  15

Pro Ala Gly Gly
            20
```

```
<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 56

Gly Gly Leu Tyr Glu Cys Arg Met Gly Pro Met Thr Xaa Val Cys Arg
  1               5                  10                  15

Pro Gly Gly Gly
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 57

Gly Gly Asp Tyr Thr Cys Arg Met Gly Pro Ile Thr Xaa Ile Cys Thr
  1               5                  10                  15

Lys Ala Gly Gly
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 58

Gly Gly Val Tyr Ser Cys Arg Met Gly Pro Thr Thr Xaa Glu Cys Asn
  1               5                  10                  15

Arg Tyr Val Gly
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 59

Gly Gly Ala Tyr Leu Cys His Met Gly Pro Ile Thr Xaa Val Cys Arg
```

```
                1               5                  10                  15
Pro Gln Gly Gly
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 60

Gly Gly Glu Tyr Ser Cys Arg Met Gly Pro Asn Thr Xaa Val Cys Lys
  1               5                  10                  15
Pro Val Gly Gly
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 61

Gly Gly Leu Tyr Leu Cys Arg Met Gly Pro Val Thr Xaa Glu Cys Gln
  1               5                  10                  15
Pro Arg Gly Gly
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 62

Gly Gly Leu Tyr Thr Cys Arg Met Gly Pro Ile Thr Xaa Val Cys Leu
  1               5                  10                  15
Leu Pro Gly Gly
            20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
```

<223> OTHER INFORMATION: 1-Nal

<400> SEQUENCE: 63

Gly Gly Leu Tyr Thr Cys Arg Met Gly Pro Val Thr Xaa Val Cys Thr
 1               5                  10                  15

Gly Ala Gly Gly
        20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 64

Gly Gly Val Tyr Lys Cys Arg Met Gly Pro Leu Thr Xaa Glu Cys Arg
 1               5                  10                  15

Pro Thr Gly Gly
        20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 65

Gly Gly Asp Tyr Asn Cys Arg Phe Gly Pro Leu Thr Xaa Val Cys Lys
 1               5                  10                  15

Pro Ser Gly Gly
        20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 66

Gly Gly Ser Tyr Leu Cys Arg Phe Gly Pro Thr Thr Xaa Leu Cys Ser
 1               5                  10                  15

Ser Ala Gly Gly
        20

<210> SEQ ID NO 67
<211> LENGTH: 20
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 67

Gly Gly Ser Tyr Leu Cys Arg Met Gly Pro Thr Thr Xaa Val Cys Thr
 1               5                  10                  15

Arg Met Gly Gly
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 68

Gly Gly Ser Tyr Leu Cys Arg Phe Gly Pro Thr Thr Xaa Leu Cys Thr
 1               5                  10                  15

Gln Arg Gly Gly
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 69

Gly Gly Trp Val Thr Cys Arg Met Gly Pro Ile Thr Xaa Val Cys Gly
 1               5                  10                  15

Val His Gly Gly
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 70

Gly Gly Gln Leu Leu Cys Gly Ile Gly Pro Ile Thr Xaa Val Cys Arg
 1               5                  10                  15

Trp Val Gly Gly
            20

```
<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 71

Gly Gly Lys Tyr Ser Cys Phe Met Gly Pro Thr Thr Xaa Val Cys Ser
1               5                   10                  15

Pro Val Gly Arg Gly Val
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 72

Gly Gly Trp Val Tyr Cys Arg Ile Gly Pro Ile Thr Xaa Val Cys Asp
1               5                   10                  15

Thr Asn Gly Gly
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 73

Gly Gly Met Tyr Tyr Cys Arg Met Gly Pro Met Thr Xaa Val Cys Lys
1               5                   10                  15

Gly Ala Gly Gly
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 74

Gly Gly Thr Thr Gln Cys Trp Ile Gly Pro Ile Thr Xaa Val Cys Arg
1               5                   10                  15
```

Ala Arg Gly Gly
            20

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 75

Gly Gly Pro Tyr His Cys Arg Met Gly Pro Ile Thr Xaa Val Cys Gly
 1               5                  10                  15

Pro Val Gly Gly
            20

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 76

Gly Gly Glu Tyr Arg Cys Arg Met Gly Pro Ile Ser Xaa Val Cys Ser
 1               5                  10                  15

Pro Gln Gly Gly
            20

<210> SEQ ID NO 77
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 77

Gly Gly Asn Tyr Thr Cys Arg Phe Gly Pro Leu Thr Xaa Glu Cys Thr
 1               5                  10                  15

Pro Gln Gly Gly Gly Ala
            20

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 78

Gly Gly Ser Trp Asp Cys Arg Ile Gly Pro Ile Thr Xaa Val Cys Lys
1               5                   10                  15
Trp Ser Gly Gly
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 79

Gly Gly Leu Tyr Leu Cys Arg Met Gly Pro Gln Thr Xaa Met Cys Gln
1               5                   10                  15
Pro Gly Gly Gly
            20

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 80

Gly Gly Asp Tyr Val Cys Arg Met Gly Pro Met Thr Xaa Val Cys Ala
1               5                   10                  15
Pro Tyr Gly Arg
            20

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 81

Gly Gly Trp Tyr Ser Cys Leu Met Gly Pro Met Thr Xaa Val Cys Lys
1               5                   10                  15
Ala His Arg Gly
            20

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (13)
<223> OTHER INFORMATION: 1-Nal

<400> SEQUENCE: 82

Gly Gly Lys Tyr Tyr Cys Trp Met Gly Pro Met Thr Xaa Val Cys Ser
1               5                   10                  15

Pro Ala Gly Gly
            20

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 83

Gly Gly Tyr Val Met Cys Arg Ile Gly Pro Ile Thr Xaa Val Cys Asp
1               5                   10                  15

Ile Pro Gly Gly
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 84

Gly Ser Cys Leu Gln Cys Cys Ile Gly Pro Ile Thr Xaa Val Cys Arg
1               5                   10                  15

His Ala Gly Gly
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 85

Gly Gly Asn Tyr Phe Cys Arg Met Gly Pro Ile Thr Xaa Val Cys Gln
1               5                   10                  15

Arg Ser Val Gly
            20

<210> SEQ ID NO 86
```

-continued

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 86

Gly Gly Glu Tyr Ile Cys Arg Met Gly Pro Leu Thr Xaa Glu Cys Lys
  1               5                  10                  15

Arg Thr Gly Gly
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 87

Gly Gly Leu Tyr Ala Cys Arg Met Gly Pro Ile Thr Xaa Val Cys Lys
  1               5                  10                  15

Tyr Met Ala Gly
            20

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 88

Gly Gly Gln Tyr Leu Cys Thr Phe Gly Pro Ile Thr Xaa Leu Cys Arg
  1               5                  10                  15

Gly Ala Gly Gly
            20

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 89

Gly Gly Tyr Thr Thr Cys Arg Met Gly Pro Ile Thr Xaa Val Cys Ser
  1               5                  10                  15
```

Ala His Gly Gly
        20

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 90

Gly Gly Thr Tyr Lys Cys Trp Met Gly Pro Met Thr Xaa Val Cys Arg
 1               5                  10                  15

Pro Val Gly Gly
        20

<210> SEQ ID NO 91
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Asn Tyr Tyr Cys Arg Phe Gly Pro Ile Thr Phe Glu Cys His
 1               5                  10                  15

Pro Thr Gly Gly
        20

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 92

Gly Gly Glu Tyr Leu Cys Arg Met Gly Pro Met Thr Xaa Val Cys Thr
 1               5                  10                  15

Pro Val Gly Gly
        20

<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)
<223> OTHER INFORMATION: 1-Nal

<400> SEQUENCE: 93

```
Gly Gly Leu Tyr Thr Cys Arg Met Gly Pro Ile Thr Xaa Val Cys Leu
 1               5                  10                  15
Pro Ala Gly Gly
            20
```